United States Patent
Spohn et al.

(10) Patent No.: US 11,389,585 B2
(45) Date of Patent: Jul. 19, 2022

(54) PRESSURE JACKET HAVING SYRINGE RETAINING ELEMENT

(71) Applicant: BAYER HEALTHCARE LLC, Whippany, NJ (US)

(72) Inventors: Michael Spohn, Fenelton, PA (US); Kevin Cowan, Allison Park, PA (US); Barry Tucker, Verona, PA (US); Michael McDermott, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 311 days.

(21) Appl. No.: 16/331,366

(22) PCT Filed: Sep. 14, 2017

(86) PCT No.: PCT/US2017/051473
§ 371 (c)(1),
(2) Date: Mar. 7, 2019

(87) PCT Pub. No.: WO2018/053074
PCT Pub. Date: Mar. 22, 2018

(65) Prior Publication Data
US 2019/0192770 A1    Jun. 27, 2019

Related U.S. Application Data

(60) Provisional application No. 62/395,684, filed on Sep. 16, 2016.

(51) Int. Cl.
*A61M 5/145* (2006.01)
*A61M 5/00* (2006.01)

(52) U.S. Cl.
CPC ........ *A61M 5/14546* (2013.01); *A61M 5/007* (2013.01); *A61M 2005/14553* (2013.01)

(58) Field of Classification Search
CPC ............. A61M 5/14546; A61M 5/007; A61M 2005/14553; A61M 5/152;
(Continued)

(56) References Cited

U.S. PATENT DOCUMENTS

| 352,715 | A | 11/1886 | Sandmark |
| 798,093 | A | 8/1905 | Edward |

(Continued)

FOREIGN PATENT DOCUMENTS

| EP | 1086661 A2 | 3/2001 |
| EP | 2098258 A1 | 9/2009 |

(Continued)

OTHER PUBLICATIONS

"International Preliminary Report on Patentability and Written Opinion from PCT Application No. PCT/US2017/051473", dated Mar. 28, 2019.

*Primary Examiner* — Amber R Stiles
*Assistant Examiner* — Avery Smale
(74) *Attorney, Agent, or Firm* — Joseph L. Kent; David Schramm; James R. Stevenson

(57) ABSTRACT

A pressure jacket configured for connecting to an injector head of a fluid injector has an open distal end, an open proximal end, and a sidewall defining a throughbore extending between the distal end and the proximal end along a longitudinal axis. The throughbore is configured for receiving at least a portion of a syringe. The pressure jacket has at least one syringe retaining element positioned at least partially within the throughbore. The at least one syringe retaining element is configured for engaging at least a portion of the syringe during pressurized delivery of fluid from the syringe to prevent or limit a distal movement of the syringe relative to the pressure jacket.

13 Claims, 28 Drawing Sheets

(58) Field of Classification Search
CPC .. A61M 5/14566; A61M 5/142; A61M 5/145; A61M 5/14; A61M 2005/1401; A61M 2205/19

See application file for complete search history.

(56) References Cited

U.S. PATENT DOCUMENTS

| | | | |
|---|---|---|---|
| 937,029 A | 10/1909 | Blessing et al. | |
| 2,514,575 A | 7/1950 | Hein et al. | |
| 2,667,163 A | 1/1954 | Smith | |
| 2,667,164 A | 1/1954 | Smith | |
| 2,667,165 A | 1/1954 | Smith | |
| 2,667,872 A | 2/1954 | Smith | |
| 2,672,866 A | 3/1954 | Kater | |
| 2,673,561 A | 3/1954 | Peterson, Jr. | |
| 2,688,963 A | 9/1954 | Smith | |
| 2,688,964 A | 9/1954 | Smith | |
| 2,690,179 A | 9/1954 | Fox | |
| 2,717,598 A | 9/1955 | Krasno | |
| 2,805,662 A | 9/1957 | Lawshe et al. | |
| 2,911,972 A | 11/1959 | Elinger | |
| 2,935,067 A | 5/1960 | Bouet | |
| 2,950,717 A | 8/1960 | Bonet | |
| 3,155,281 A | 11/1964 | Stracey | |
| 3,161,194 A | 12/1964 | Chapman | |
| 3,161,195 A | 12/1964 | Taylor et al. | |
| 3,172,577 A | 3/1965 | Hartung | |
| 3,190,619 A | 6/1965 | Penney et al. | |
| 3,231,139 A | 1/1966 | Bouet | |
| 3,301,293 A | 1/1967 | Santelli | |
| 3,340,869 A | 9/1967 | Bane | |
| 3,390,821 A | 7/1968 | Mullan | |
| 3,411,503 A | 11/1968 | Santomieri | |
| 3,442,424 A | 5/1969 | Sam et al. | |
| 3,471,058 A | 10/1969 | Peter et al. | |
| 3,473,524 A | 10/1969 | John | |
| 3,474,844 A | 10/1969 | Rudolph et al. | |
| 3,506,163 A | 4/1970 | James et al. | |
| 3,557,788 A | 1/1971 | Swartz | |
| 3,613,963 A | 10/1971 | Berkmuller | |
| 3,618,846 A | 11/1971 | Poli | |
| 3,826,409 A | 7/1974 | Chilcoate | |
| 3,873,003 A | 3/1975 | Seiferth et al. | |
| 3,938,514 A | 2/1976 | Boucher et al. | |
| 4,035,461 A | 7/1977 | Korth | |
| 4,044,836 A | 8/1977 | Martin et al. | |
| 4,064,879 A | 12/1977 | Leibinsohn | |
| 4,066,080 A | 1/1978 | Sneider | |
| 4,131,217 A | 12/1978 | Sandegren | |
| 4,136,802 A | 1/1979 | Mascia et al. | |
| 4,171,698 A | 10/1979 | Genese | |
| 4,349,129 A | 9/1982 | Amneus | |
| 4,392,491 A | 7/1983 | Takasugi et al. | |
| 4,411,656 A | 10/1983 | Cornett, III | |
| 4,526,296 A | 7/1985 | Berger et al. | |
| 4,753,638 A | 6/1988 | Peters | |
| 4,773,458 A | 9/1988 | Touzani | |
| 4,850,807 A | 7/1989 | Frantz | |
| 5,000,739 A | 3/1991 | Kulisz et al. | |
| 5,201,438 A | 4/1993 | Norwood | |
| 5,209,372 A | 5/1993 | Norwood | |
| 5,236,204 A | 8/1993 | Hempel | |
| 5,238,150 A | 8/1993 | Williams | |
| 5,240,130 A | 8/1993 | Osbakk | |
| 5,242,422 A | 9/1993 | Schneberger et al. | |
| 5,269,428 A | 12/1993 | Gilbert | |
| 5,333,761 A | 8/1994 | Davis et al. | |
| 5,353,961 A | 10/1994 | Debush | |
| 5,370,250 A | 12/1994 | Gilbert | |
| 5,383,858 A | 1/1995 | Reilly et al. | |
| 5,397,157 A | 3/1995 | Hempel et al. | |
| 5,573,129 A | 11/1996 | Nagata et al. | |
| 5,584,413 A | 12/1996 | Jung | |
| 5,592,948 A | 1/1997 | Gatten | |
| 5,609,580 A | 3/1997 | Kwiatkowski et al. | |
| 5,615,791 A | 4/1997 | Matelot et al. | |
| 5,638,995 A | 6/1997 | Mazda | |
| 5,683,369 A | 11/1997 | Tsukada | |
| 5,758,789 A | 6/1998 | Shin et al. | |
| 5,794,107 A | 8/1998 | Russell | |
| 5,827,233 A | 10/1998 | Futagawa et al. | |
| 5,836,922 A | 11/1998 | Hansen et al. | |
| 5,873,861 A | 2/1999 | Hitchins et al. | |
| 5,899,889 A | 5/1999 | Futagawa et al. | |
| RE36,377 E | 11/1999 | Gilbert | |
| 5,979,326 A | 11/1999 | Ohinata | |
| 6,054,194 A | 4/2000 | Kane | |
| 6,062,437 A | 5/2000 | Mascitelli | |
| 6,077,252 A | 6/2000 | Siegel | |
| 6,105,815 A | 8/2000 | Mazda | |
| 6,142,976 A | 11/2000 | Kubo et al. | |
| 6,216,915 B1 | 4/2001 | Harman et al. | |
| 6,224,577 B1 | 5/2001 | Dedola et al. | |
| 6,250,505 B1 | 6/2001 | Petit | |
| 6,315,761 B1 | 11/2001 | Shcherbina et al. | |
| 6,319,235 B1 | 11/2001 | Yoshino | |
| 6,322,535 B1 | 11/2001 | Hitchins et al. | |
| 6,332,876 B1 | 12/2001 | Poynter et al. | |
| 6,485,471 B1 | 11/2002 | Ziviiz et al. | |
| 6,558,358 B2 | 5/2003 | Rosoff et al. | |
| 6,578,738 B1 | 6/2003 | Keller | |
| 6,620,134 B1 | 9/2003 | Trombley, III et al. | |
| 6,634,524 B1 | 10/2003 | Helmenstein | |
| 6,652,489 B2 | 11/2003 | Trocki et al. | |
| 6,702,143 B2 | 3/2004 | Wang | |
| 6,716,195 B2* | 4/2004 | Nolan, Jr | A61M 5/1456 604/131 |
| 6,773,417 B2 | 8/2004 | Fitzgibbons et al. | |
| 6,840,164 B2 | 1/2005 | Eastman | |
| 6,866,039 B1 | 3/2005 | Wright et al. | |
| 6,869,419 B2 | 3/2005 | Dragan et al. | |
| RE38,770 E | 8/2005 | Gilbert | |
| 6,974,443 B2* | 12/2005 | Reilly | B05C 17/00596 604/131 |
| 7,004,213 B2 | 2/2006 | Hansen | |
| 7,011,650 B2 | 3/2006 | Rosoff et al. | |
| 7,192,549 B2 | 3/2007 | Hansen | |
| 7,250,039 B2 | 7/2007 | Fitzgerald | |
| 7,309,463 B2 | 12/2007 | Hansen | |
| 7,513,378 B2 | 4/2009 | Mori et al. | |
| 7,553,294 B2 | 6/2009 | Lazzaro et al. | |
| 7,563,249 B2 | 7/2009 | Schriver et al. | |
| 7,604,623 B2 | 10/2009 | Brunner et al. | |
| 7,666,169 B2 | 2/2010 | Cowan et al. | |
| 7,802,691 B2 | 9/2010 | Musalek et al. | |
| 8,945,051 B2 | 2/2015 | Schriver et al. | |
| 9,173,995 B1 | 11/2015 | Tucker et al. | |
| 9,180,252 B2 | 11/2015 | Gelblum et al. | |
| 9,199,033 B1 | 12/2015 | Cowan et al. | |
| 9,474,857 B2 | 10/2016 | Riley et al. | |
| 10,046,106 B2 | 8/2018 | Cowan et al. | |
| 10,105,491 B2 | 10/2018 | Gelblum et al. | |
| 10,124,110 B2 | 11/2018 | Dedig et al. | |
| 10,507,319 B2 | 12/2019 | Haury et al. | |
| 10,583,256 B2 | 3/2020 | Berry et al. | |
| 10,933,190 B2 | 3/2021 | Berry et al. | |
| 2010/0091361 A1 | 4/2010 | Yuuki | |
| 2012/0020911 A1 | 1/2012 | Seliktar et al. | |
| 2012/0209111 A1 | 8/2012 | Cowan et al. | |
| 2012/0253291 A1 | 10/2012 | Ivosevic et al. | |
| 2013/0023048 A1 | 1/2013 | Kim et al. | |
| 2013/0211248 A1 | 8/2013 | Cowan et al. | |
| 2013/0281940 A1 | 10/2013 | Gelblum et al. | |
| 2017/0035974 A1 | 2/2017 | Berry et al. | |

FOREIGN PATENT DOCUMENTS

| | | |
|---|---|---|
| EP | 3057648 A1 | 8/2016 |
| FR | 1288915 A | 3/1962 |
| GB | 2214819 A | 9/1989 |
| GB | 2374143 A | 10/2002 |
| WO | 9221391 A1 | 12/1992 |
| WO | 9526211 A1 | 10/1995 |
| WO | 9707841 A2 | 3/1997 |

(56) References Cited

FOREIGN PATENT DOCUMENTS

| WO | 0137903 A2 | 5/2001 | |
|---|---|---|---|
| WO | 0204049 A1 | 1/2002 | |
| WO | WO-2009038955 A1 * | 3/2009 | ........ A61M 5/14546 |
| WO | 2010004206 A2 | 1/2010 | |
| WO | 2010014654 A1 | 2/2010 | |
| WO | 2012061140 A1 | 5/2012 | |
| WO | 2012155035 A1 | 11/2012 | |
| WO | 2014027009 A1 | 2/2014 | |
| WO | 2015058088 A1 | 4/2015 | |
| WO | 2015066506 A2 | 5/2015 | |
| WO | 2015164783 A1 | 10/2015 | |
| WO | 2016058946 A1 | 4/2016 | |
| WO | 2016069711 A1 | 5/2016 | |
| WO | 2016069714 A1 | 5/2016 | |
| WO | 2016112163 A1 | 7/2016 | |
| WO | 2016172467 A1 | 10/2016 | |
| WO | 2016191485 A1 | 12/2016 | |
| WO | 2017040154 A1 | 3/2017 | |
| WO | 2020055818 A1 | 3/2020 | |

* cited by examiner

PRESSURE JACKET HAVING SYRINGE RETAINING ELEMENT

CROSS-REFERENCE TO RELATED APPLICATION

This application is a 371 national phase application of PCT International Application No. PCT/US2017/051473, filed Sep. 14, 2017, and claims the benefit of U.S. Provisional Patent Application No. 62/395,684, filed Sep. 16, 2016, the disclosures of which are incorporated herein by reference in their entirety.

BACKGROUND OF THE DISCLOSURE

Field of the Disclosure

The present disclosure relates generally to fluid injectors having at least one pressure jacket and to syringes for use with the fluid injectors having the at least one pressure jacket. More specifically, the disclosure relates to fluid injectors having at least one pressure jacket with one or more syringe retaining elements for restraining axial movement of the syringe relative to the at least one pressure jacket during an injection procedure.

Description of the Related Art

In many medical diagnostic and therapeutic procedures, a medical practitioner, such as a physician, injects a patient with one or more medical fluids. In recent years, a number of injector-actuated syringes and powered fluid injectors for pressurized injection of medical fluids, such as a contrast solution (often referred to simply as "contrast"), a flushing agent, such as saline, and other medical fluids, have been developed for use in procedures such as angiograph, computed tomography (CT), ultrasound, magnetic resonance imaging (MRI), positron emission tomography (PET), and other imaging procedures. In general, these fluid injectors are designed to deliver a preset amount of one or more fluids at a preset pressure and/or flow rate.

Typically, a fluid injector has at least one drive member, such as at least one piston, that connects to a syringe plunger within the syringe. The syringe generally includes a rigid barrel with the syringe plunger being slidably disposed within the barrel. The piston drives the plunger in a proximal and/or distal direction relative to a longitudinal axis of the barrel to draw fluid into the syringe barrel or deliver the fluid from the syringe barrel.

Syringes for use with fluid injectors may be made of various medical-grade plastic materials with a certain minimum wall thickness. Syringe thickness is an important design factor, as pressures of up to 1200 psi may be used during an injection procedure. During certain injection procedures, the syringe itself is typically not capable of withstanding the high pressure due to excessive radial expansion under such pressure. Fluid injectors having at least one pressure jacket have been developed for enclosing at least a portion of the syringe w ile in use and preventing radial expansion of the syringe due to buildup of fluid pressure within the syringe. Such pressure jackets are designed to withstand the high injection pressures without appreciable radial expansion.

Certain existing pressure jackets have a one-piece cylindrical design, where the syringe is inserted into the pressure jacket from the front (distal) end of the pressure jacket. The neck of the syringe may protrude from the distal end of the pressure jacket such that the syringe may be connected to fluid lines leading to the patient. A proximal end of the pressure jacket is typically retained on the fluid injector by a coupling member. During an injection procedure, an exterior wall of the syringe expands against an interior wall of the pressure jacket due to the forces that act on the syringe in a radially outward direction. Additionally, the syringe may experience significant axial movement during a high pressure injection due to the axial movement of the piston acting on the syringe. Such axial movement of the syringe is undesirable and may lead to inaccurate volume delivery. To prevent the axial movement of the syringe within the pressure jacket, a holding bracket or distal locking cap may be provided on the pressure jacket and/or the fluid injector.

While front loading, pressure jacketed fluid injector systems are known in the art, improvements in the design of such pressure jacketed fluid injector systems, and also in the design of syringes used in both pressure jacketed and non-pressure jacketed injector systems, are and continue to be highly desirable. In particular, it would be desirable to provide improved pressure jackets configured for preventing or limiting axial movement of the syringe during an injection procedure.

SUMMARY OF DISCLOSURE

The present disclosure generally relates to fluid injectors having at least one pressure jacket with one or more syringe retaining elements for preventing or limiting axial movement of the syringe relative to the pressure jacket during an injection procedure.

In some examples of the present disclosure, a pressure jacket may be configured for connecting to an injector head of a fluid injector. The pressure jacket may have an open distal end, an open proximal end, and a sidewall defining a throughbore extending between the distal end and the proximal end along a longitudinal axis. The throughbore may be configured for receiving at least a portion of a syringe. The pressure jacket may have at least one syringe retaining element positioned at least partially within the throughbore, and at least one actuation mechanism operatively connected to the at least one syringe retaining element. The at least one actuation mechanism may be configured to move the at least one syringe retaining element relative to the pressure jacket between a disengaged position to permit a distal/proximal movement of the syringe within the throughbore and an engaged position to limit or prevent the distal movement of the syringe during pressurized delivery of fluid from the syringe.

In some examples of the present disclosure, the at least one actuation mechanism may be axially or radially movable relative to the pressure jacket to move the at least one syringe retaining element between the disengaged position and the engaged position. The at least one actuation mechanism may be biased to the disengaged position by a biasing member. The at least one syringe retaining element may be a plurality of radially extendable and retractable fingers. The plurality of radially extendable and retractable fingers may extend radially inward from an interior surface of the sidewall of the pressure jacket in the engaged position and retract into a pocket recessed into the interior surface of the sidewall of the pressure jacket in the disengaged position. A distal end of at least a portion of the plurality of radially extendable and retractable fingers may have a retaining lip or other engagement feature configured to engage at least a portion of a distal end of the syringe when the plurality of radially extendable and retractable fingers are in the engaged position.

In some examples of the present disclosure, the at least one syringe retaining element may be a spring having a first end connected to at least a portion of the pressure jacket and a second end connected to the at least one actuation mechanism. The spring may biased to the engaged position. The at least one syringe retaining element may be a compressible ring positioned within a pocket recessed into an interior surface of the pressure jacket. The at least one actuation mechanism may compress the compressible ring in the engaged position to move at least a portion of the compressible ring radially inward from the interior surface of the sidewall of the pressure jacket. The at least one syringe retaining element may be a sleeve positioned within the throughbore of the pressure jacket between an interior surface of the sidewall of the pressure jacket and an exterior surface of the syringe.

In some examples of the present disclosure, a pressure jacket configured for connecting to an injector head of a fluid injector may have an open distal end, an open proximal end, and a sidewall defining a throughbore extending between the distal end and the proximal end along a longitudinal axis. The throughbore may be configured for receiving at least a portion of a syringe. The pressure jacket may have at least one syringe retaining element positioned at least partially within the throughbore. The at least one syringe retaining element may be configured for engaging at least a portion of the syringe during pressurized delivery of fluid from the syringe to prevent or limit a distal movement of the syringe relative to the pressure jacket.

In some examples of the present disclosure, the at least one syringe retaining element may be at least one expansion pocket recessed radially outward into an interior surface of the sidewall of the pressure jacket. A volume of the at least one expansion pocket may be selected to prevent plastic yield of a sidewall of the syringe during the pressurized delivery of fluid from the syringe exceeding a predetermined threshold pressure. A volume of the at least one expansion pocket may be selected to maintain a predetermined axial restraining force due to radial expansion of at least a portion of a sidewall of the syringe into the at least one expansion pocket during the pressurized delivery of fluid from the syringe. The at least one expansion pocket may be circumferentially continuous or discontinuous around a circumference of the interior surface of the sidewall of the pressure jacket. The at least one expansion pocket may be a plurality of expansion pockets axially offset from each other. The at least one expansion pocket may be helical.

In some examples of the present disclosure, the at least one syringe retaining element may be at least one protrusion protruding radially inward from an interior surface of the sidewall of the pressure jacket. The at least one protrusion may be circumferentially continuous or discontinuous around a circumference of the inner surface of the sidewall of the pressure jacket. The at least one protrusion may be a plurality of protrusions axially offset from each other. The at least one protrusion may be helical.

In some examples of the present disclosure, a fluid injector for delivering fluid to a patient may have at least one injector head, and at least one pressure jacket removably connected to the at least one injector head. The at least one pressure jacket may have an open distal end, an open proximal end, and a sidewall defining a throughbore extending between the distal end and the proximal end along a longitudinal axis. The throughbore may be configured for receiving at least a portion of a syringe. The pressure jacket may have at least one syringe retaining element positioned at least partially within the throughbore. The at least one syringe retaining element may be configured for engaging at least a portion of the syringe during pressurized delivery of fluid from the syringe to prevent or limit a distal movement of the syringe relative to the at least one pressure jacket.

Various aspects of fluid injectors having at least one pressure jacket with one or more syringe retaining elements for preventing or limiting axial movement of the syringe relative to the at least one pressure jacket during an injection procedure are disclosed in one or more of the following numbered clauses:

Clause 1. A pressure jacket configured for removably connecting to an injector head of a fluid injector, the pressure jacket comprising: an open distal end, an open proximal end, and a sidewall defining a throughbore extending between the distal end and the proximal end along a longitudinal axis, the throughbore configured for receiving at least a portion of a syringe; and at least one syringe retaining element positioned at least partially within the throughbore; wherein the at least one syringe retaining element is configured for engaging at least a portion of the syringe during pressurized delivery of fluid from the syringe to prevent or limit a distal movement of the syringe relative to the pressure jacket.

Clause 2. The pressure jacket of clause 1, wherein the at least one syringe retaining element comprises at least one expansion pocket recessed radially outward into an interior surface of the sidewall of the pressure jacket.

Clause 3. The pressure jacket of any of clauses 1-2, wherein a volume of the at least one expansion pocket is selected to prevent plastic yield of a sidewall of the syringe during the pressurized delivery of fluid from the syringe exceeding a predetermined threshold pressure.

Clause 4. The pressure jacket of any of clauses 1-3, wherein a volume of the at least one expansion pocket is selected to maintain a predetermined axial restraining force due to radial expansion of at least a portion of a sidewall of the syringe into the at least one expansion pocket during the pressurized delivery of fluid from the syringe.

Clause 5. The pressure jacket of any of clauses 1-4, wherein the at least one expansion pocket is circumferentially continuous or discontinuous around a circumference of the interior surface of the sidewall of the pressure jacket.

Clause 6. The pressure jacket of any of clauses 1-5, wherein the at least one expansion pocket is a plurality of expansion pockets axially offset from each other.

Clause 7. The pressure jacket of any of clauses 1-6, wherein the at least one expansion pocket is helical.

Clause 8. The pressure jacket of any of clauses 1-7, wherein the at least one syringe retaining element comprises at least one protrusion protruding radially inward from an interior surface of the sidewall of the pressure jacket.

Clause 9. The pressure jacket of any of clauses 1-8, wherein the at least one protrusion is circumferentially continuous or discontinuous around a circumference of the interior surface of the sidewall of the pressure jacket.

Clause 10. A pressure jacket configured for removably connecting to an injector head of a fluid injector, the pressure jacket comprising: an open distal end, an open proximal end, and a sidewall defining a throughbore extending between the distal end and the proximal end along a longitudinal axis, the throughbore configured for receiving at least a portion of a syringe; at least one syringe retaining element positioned at least partially within the throughbore; and at least one actuation mechanism operatively connected to the at least one syringe retaining element, wherein the at least one actuation mechanism is configured to move the at least one syringe retaining element relative to the pressure jacket between a disengaged position to permit a distal movement of the syringe within the throughbore and an engaged position to limit or prevent the distal movement of the syringe during pressurized delivery of fluid from the syringe.

Clause 11. The pressure jacket of clause 10, wherein the at least one actuation mechanism is axially or radially movable relative to the pressure jacket to move the at least one syringe retaining element between the disengaged position and the engaged position.

Clause 12. The pressure jacket of clause 10 or clause 11, wherein the at least one actuation mechanism is biased to the disengaged position by a biasing member.

Clause 13. The pressure jacket of any of clauses 10-12, wherein the at least one syringe retaining element is a plurality of radially extendable and retractable fingers, wherein the plurality of radially extendable and retractable fingers extend radially inward from an interior surface of the sidewall of the pressure jacket in the engaged position and retract into a pocket recessed into the interior surface of the sidewall of the pressure jacket in the disengaged position.

Clause 14. The pressure jacket of any of clauses 10-13, wherein a distal end of at least a portion of the plurality of radially extendable and retractable fingers has a retaining lip configured to engage at least a portion of a distal end of the syringe when the plurality of radially extendable and retractable fingers are in the engaged position.

Clause 15. The pressure jacket of any of clauses 10-14, wherein the at least one syringe retaining element comprises a spring having a first end connected to at least a portion of the pressure jacket and a second end connected to the at least one actuation mechanism.

Clause 16. The pressure jacket of any of clauses 10-15, wherein the spring is biased to the engaged position.

Clause 17. The pressure jacket of any of clauses 10-16, wherein the at least one syringe retaining element comprises a compressible ring positioned within a pocket recessed into an interior surface of the sidewall of the pressure jacket.

Clause 18. The pressure jacket of any of clauses 10-17, wherein the at least one actuation mechanism compresses the compressible ring in the engaged position to move at least a portion of the compressible ring radially inward from the interior surface of the sidewall of the pressure jacket.

Clause 19. The pressure jacket of any of clauses 10-18, wherein the at least one syringe retaining element is a sleeve positioned within the throughbore of the pressure jacket between an interior surface of the pressure jacket and an exterior surface of the syringe.

Clause 20. A fluid injector for delivering fluid to a patient, the fluid injector comprising: at least one injector head; and at least one pressure jacket connected to the at least one injector head, the at least one pressure jacket having an open distal end, an open proximal end, and a sidewall defining a throughbore extending between the distal end and the proximal end along a longitudinal axis, the throughbore configured for receiving at least a portion of a syringe; and at least one syringe retaining element positioned at least partially within the throughbore, wherein the at least one syringe retaining element is configured for engaging at least a portion of the syringe during pressurized delivery of fluid from the syringe to prevent or limit a distal movement of the syringe relative to the at least one pressure jacket.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that drawings are for the purpose of illustration and description only.

BRIEF DESCRIPTION OF THE DRAWINGS

In FIGS. 1-16, the same characters represent the same components unless otherwise indicated.

DETAILED DESCRIPTION

Figure 1:
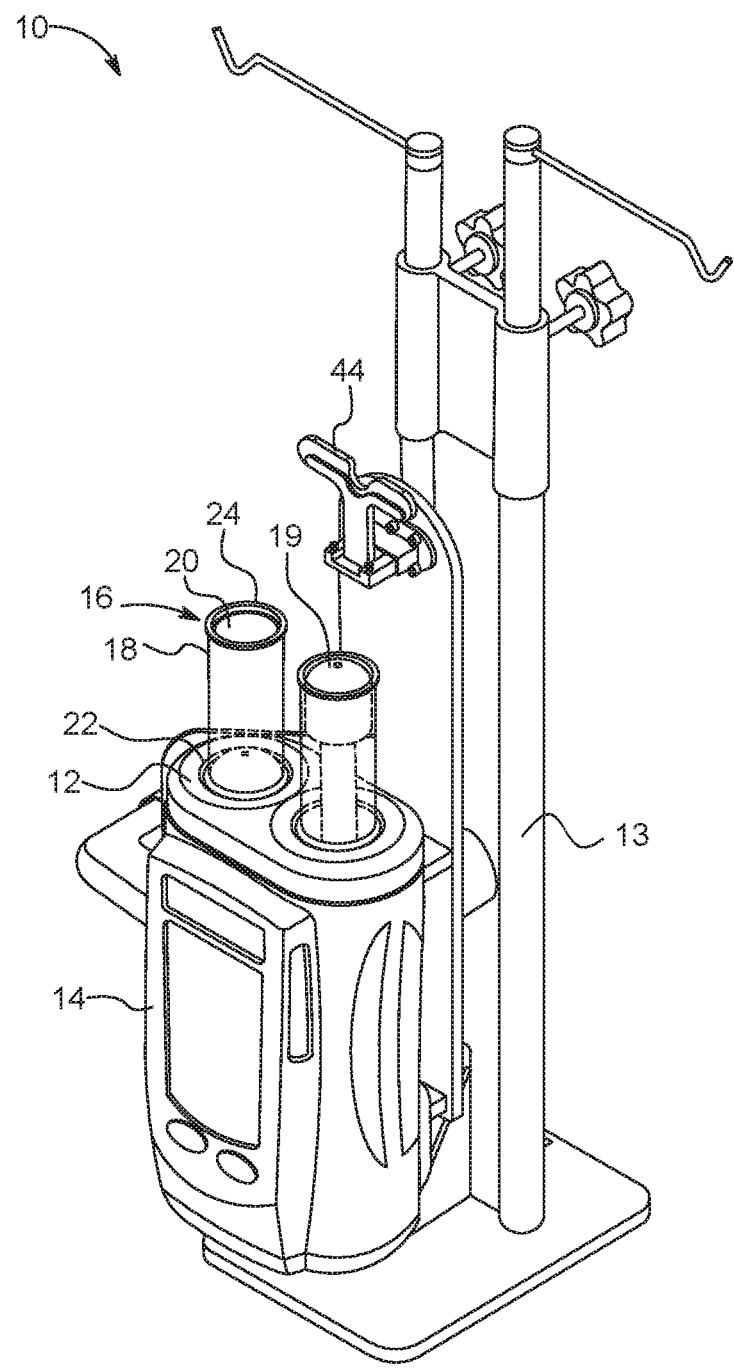
FIG. 1 is a front perspective view of a fluid injector having a pair of pressure jackets in accordance with one example of the present disclosure.

As used in the specification, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

When used in relation to a syringe and/or a pressure jacket, the term "proximal" refers to a portion of a syringe and/or a pressure jacket nearest to an injector when a syringe and/or a pressure jacket is oriented for connecting to an injector.

The term "distal" refers to a portion of a syringe and/or pressure jacket farthest away from an injector when oriented for connecting to an injector.

The term "radial" refers to a direction in a cross-sectional plane normal to a longitudinal axis of a syringe and/or pressure jacket between proximal and distal ends.

The term "circumferential" refers to a direction around an inner or outer surface of a sidewall of a syringe and/or a pressure jacket.

The term "axial" refers to a direction along a longitudinal axis of a syringe and/or a pressure jacket extending between the proximal and distal ends.

The term "flexible", when used in connection with a syringe, means that at least a portion of a syringe, such as a sidewall of a syringe, is capable of bending or being bent to change a direction in which it extends.

The terms "roll over", "rolling over", and "rolls upon itself" refer to an ability of a first portion of a syringe, such as a proximal portion of a sidewall of a syringe, to bend approximately 180° relative to a second portion of a syringe, such as a distal portion of a sidewall of a syringe, when urged by a piston of a fluid injector.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "includes" is synonymous with "comprises".

It is to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

All documents, such as but not limited to issued patents and patent applications, referred to herein, and unless otherwise indicated, are to be considered to be "incorporated by reference" in their entirety.

Referring to the drawings in which like reference characters refer to like parts throughout the several views thereof, the present disclosure is generally directed to fluid injectors having at least one pressure jacket with one or more syringe retaining elements for restraining axial movement of the syringe relative to the at least one pressure jacket during an injection procedure.

With reference to FIG. 1, a fluid injector 10 includes at least one injector head 12 and an injector housing 14. The injector head 12 may be supported on a support structure 13. In some examples, such as shown in FIG. 1, the fluid injector 10 may include two injector heads 12 arranged in a side-by-side orientation. Each injector head 12 may be formed at a front end of the injector housing 14 and may be configured for receiving and retaining at least one pressure jacket 16. While FIG. 1 illustrates the fluid injector 10 with two injector heads 12, each with a corresponding pressure jacket 16, other examples of the fluid injector 10 may include a single injector head and a corresponding pressure jacket or more than two injector heads 12 with a corresponding number of pressure jackets 16. The pressure jacket 16 may be removably attached to the injector head 12 with one or more engagement elements 25 (shown in FIG. 5A), for example the one or more engagement elements described in PCT International Publications WO 2016/069714 and WO 2016/069711, the disclosures of which are incorporated herein by this reference.

With continued reference to FIG. 1, each injector head 12 includes a drive member or piston 19, such as a reciprocally driven piston moved by a motor (not shown). Each piston 19 may be configured to extend into and from the respective injector head 12 through an opening in the front end of injector housing 14. Each piston 19 imparts a motive force to at least a portion of a syringe disposed in pressure jacket 16, as described herein.

Figure 2:
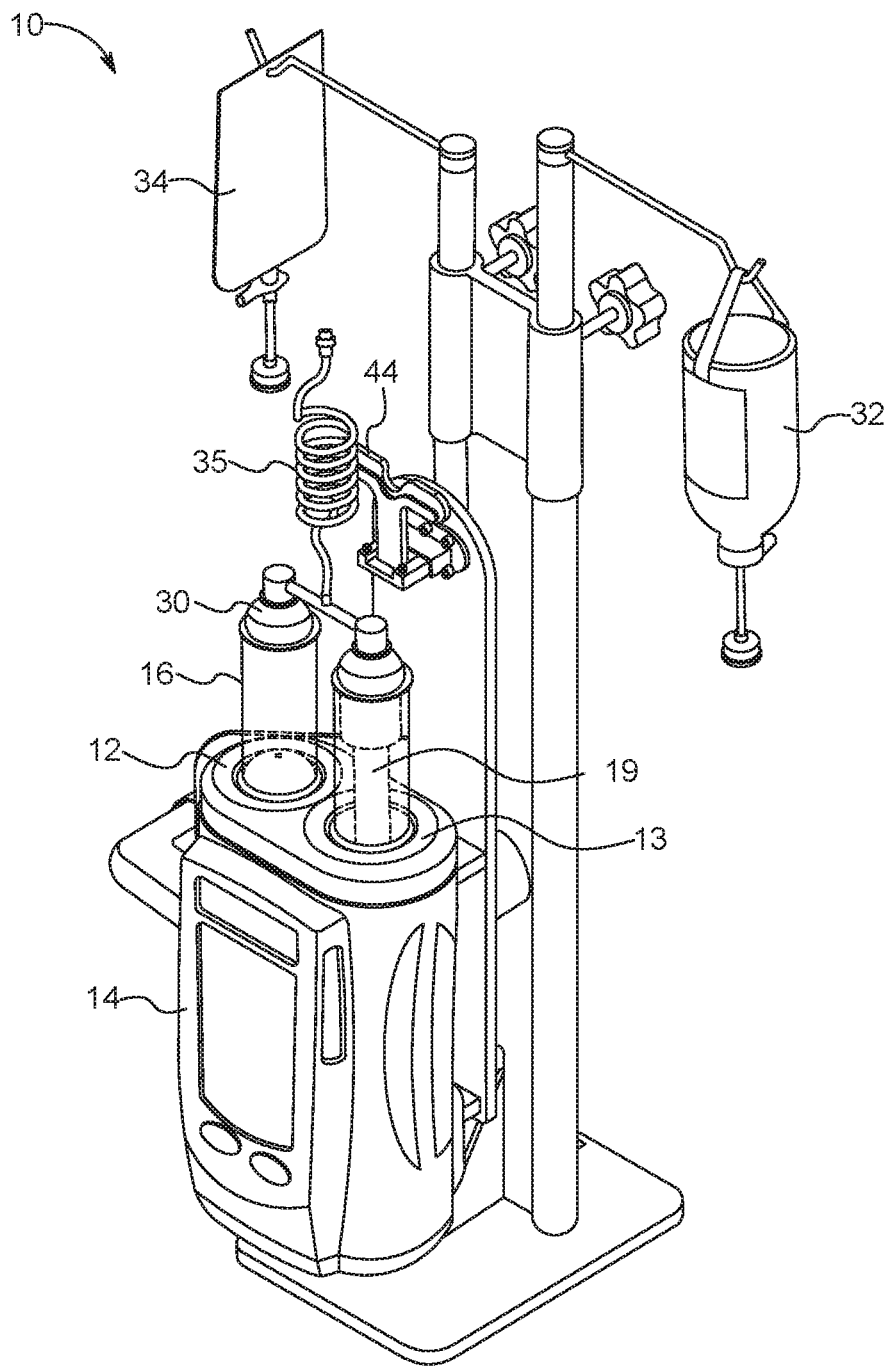
FIG. 2 is a front perspective view of the fluid injector of FIG. 1 shown with a syringe installed in each pressure jacket.

With reference to FIG. 2, the fluid injector 10 is configured to receive a syringe 30 within each pressure jacket 16. The at least one pressure jacket 16 is typically a reusable component, while the syringe 30 is typically a single-use component. The fluid injector 10 may have at least one bulk fluid source for filling the syringes 30 with fluid. The bulk fluid source may be a first bulk fluid source 32 containing a first medical fluid, such as contrast, and a second bulk fluid source 34 containing a second medical fluid, such as saline, for filling the syringes 30 with first or second fluid contained in the first and second bulk fluid sources 32, 34. At least one fluid path set 35 may be fluidly connected with a discharge end of each syringe 30 for delivering fluid from the syringes 30 through tubing connected to a catheter, needle, or other fluid delivery connection (not shown) inserted into a patient at a vascular access site. Fluid flow into and from the at least one syringe 30 may be regulated by a fluid control module (not shown). The fluid control module may operate various pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. Examples of suitable front-loading fluid injectors that may be used or modified for use with the herein-described system, including at least one pressure jacket 16 and syringe 30, are disclosed in PCT Application Publication Nos. WO 2015/164783 and WO 2016/172467, the disclosures of which are incorporated herein by reference.

In certain embodiments, suitable syringes 30 include a rolling diaphragm-type syringe as described in WO 2015/164783 and WO 2016/172467 having a flexible thin sidewall which rolls upon itself when acted upon by the piston 19 such that an outer surface of the sidewall at a folding region is folded in a radially inward direction as the piston 19 is advanced from the proximal end to the distal end and such that the out surface of the sidewall at the folding region is unfolded in a radially outward direction as the piston 19 is retracted from the proximal end to the distal end. Such rolling diaphragm syringes may be made from a suitable medical-grade plastic and have a sidewall thickness ranging from 0.01 inches-0.15 inches. Upon pressurization of the syringe 30 by distal movement of the piston 19, the fluid pressure within the rolling diaphragm syringe causes the sidewall to expand radially outward. This effect is enhanced by the relative thinness of the syringe sidewall compared to conventional syringes. As the syringe sidewall expands radially outward, it contacts the interior surface of the pressure jacket 16, which limits further expansion of the syringe sidewall, thereby preventing breaking of the syringe wall. Under the increased pressure, frictional forces between the expanded sidewall of the syringe 30 and the interior surface of the sidewall of the pressure jacket 16 prevent distal movement of the syringe 30 relative to the pressure jacket 16, thereby maintaining the syringe 30 in the pressure jacket 16. As described herein, the frictional forces between the exterior of the sidewall of the syringe 30 and the interior surface of the sidewall of the pressure jacket 16 may be modified and enhanced by incorporation of retention features into the interior surface of the sidewall of the pressure jacket 16 and/or to the exterior surface of the sidewall of the syringe 30. The increased frictional forces between these surfaces may minimize or even eliminate the need for additional structures to maintain the syringe 30 within the pressure jacket 16 during an injection procedure.

With reference to FIG. 1, the at least one pressure jacket 16 is mounted to the front end of the injector housing 14 by an attachment mechanism (not shown) that allows for removable connection of the at least one pressure jacket 16 with the injector housing 14. In some examples, the at least one pressure jacket 16 may be non-removably connected to the injector housing 14.

With reference to FIGS. 4A-4D, the at least one pressure jacket 16 may have a generally hollow cylindrical shape with a front or distal end 18 having a syringe receiving opening 20 (shown in FIG. 1) for receiving the syringe 30 into the pressure jacket 16. The at least one pressure jacket 16 further includes a rear or proximal end 22 configured to engage at least a portion of the fluid injector 10 and removably or non-removably connect the at least one pressure jacket 16 to the fluid injector 10. The at least one pressure jacket 16 has a sidewall 24 extending between the distal end 18 and the proximal end 22 along a longitudinal axis 23 of the at least one pressure jacket 16. The opening 20 at the distal end 18 of the at least one pressure jacket 16 defines a throughbore 26 that extends between the distal end 18 and the proximal end 22 along a longitudinal axis 23 of the pressure jacket 16. The at least one pressure jacket 16 has an inner diameter D1 (shown in FIG. 4A) sized to snugly but removably receive the outer diameter D2 of the syringe 30 (shown in FIG. 4A) such that the syringe 30 can be easily inserted into and removed from the throughbore 26 without interference with an interior surface 28 of the pressure jacket sidewall 24. The interior surface 28 of the pressure jacket sidewall 24 is configured to contact at least a portion of an exterior surface of the syringe 30 at least during an injection procedure wherein the syringe 30 is expanded radially outward due to fluid pressure within the syringe 30. As described herein the contact between the exterior surface of syringe 30 and interior surface 26 of the pressure jacket sidewall 24 may be frictionally enhanced but at least one syringe retaining element.

The at least one pressure jacket 16 may be made from a material capable of restraining an outward radial expansion of the syringe 30 during an injection procedure. As discussed previously, the syringe 30 itself may not be capable of withstanding the high pressures associated with certain fluid injection procedures, for example due to the sidewall thickness. The at least one pressure jacket 16 may be used to limit the radial expansion of the syringe 30 under pressure. For example, in certain embodiments, the radial expansion of the syringe sidewall under injection pressures may be limited to the inner diameter of the pressure jacket sidewall 24. In some examples, the at least one pressure jacket 16 may be made from a medical grade material, such as medical grade plastic, metal, or glass. In certain examples, the at least one pressure jacket 16 may be manufactured from a translucent or transparent material so that at least a portion of a syringe 30 may be observed through the sidewall 24 of the pressure jacket 16.

The syringe 30 is adapted for use in CT, MRI, PET, and like procedures and operable at typical operating pressures of, for example, about 10-400 psi, such as 200-400 psi, depending on the viscosity of the fluid, diameter of the fluid path, and the desired rate of injection. In some examples, the syringe 30 may be configured for use in procedures requiring pressures on the order to 1,200 psi, such as angiography. The syringe 30 may be a syringe disclosed in PCT Application Publication No. WO 2015/164783 and PCT Application Publication No. WO 2016/172467, the disclosures of which are incorporated herein by reference. In other examples, the syringe 30 may be a bladder syringe described in U.S. Patent Application Publication No. 2013/023048, or a syringe described in U.S. Pat. No. 9,180,252, the disclosures of which are incorporated herein by reference in their entirety. In other examples, the syringe 30 may be a syringe described in U.S. Pat. Nos. 5,383,858; 6,322,535; 6,652,489; 9,173,995; and 9,199,033, the disclosures of which are all incorporated by reference in their entirety.

With reference to FIGS. 4A-4D, according to certain embodiments, the syringe 30 may be a rolling diaphragm-type syringe which includes a hollow body that includes a forward or distal end 34, a rearward or proximal end 36, and a flexible sidewall 38 extending therebetween. In use, the proximal end 36 is configured for insertion into the throughbore 26 such that the sidewall 38 of the syringe 30 is surrounded by the interior surface 28 of the pressure jacket 16. At least a portion of the distal end 34 of the syringe 30 may be exposed from the distal end 18 of the pressure jacket 16. In some examples, the syringe 30 may be formed using a blow-molding technique using an injection molded preform. In other examples, the syringe 30 may be injection molded.

Figure 4A:
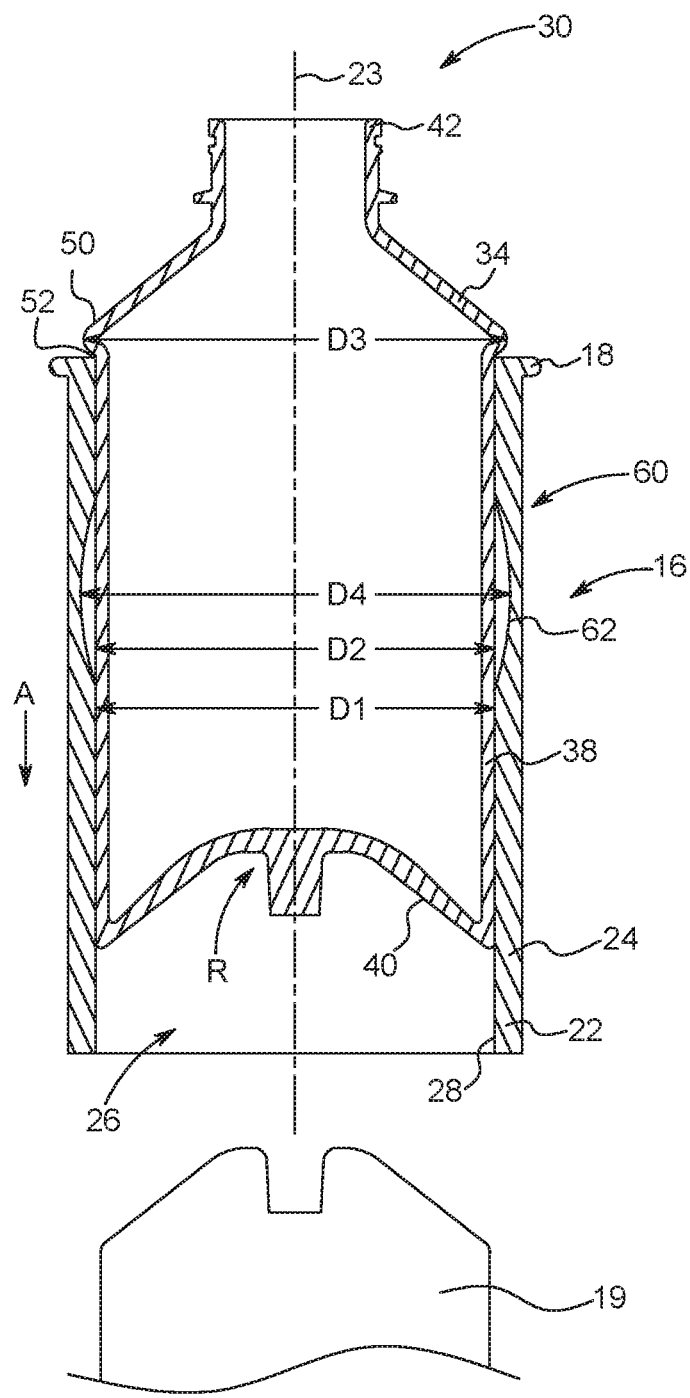
FIG. 4A is a side cross-sectional view of a syringe and a pressure jacket having a syringe retaining element in accordance with one example of the present disclosure, wherein the syringe retaining element is in a disengaged state or position.
Figure 4B:
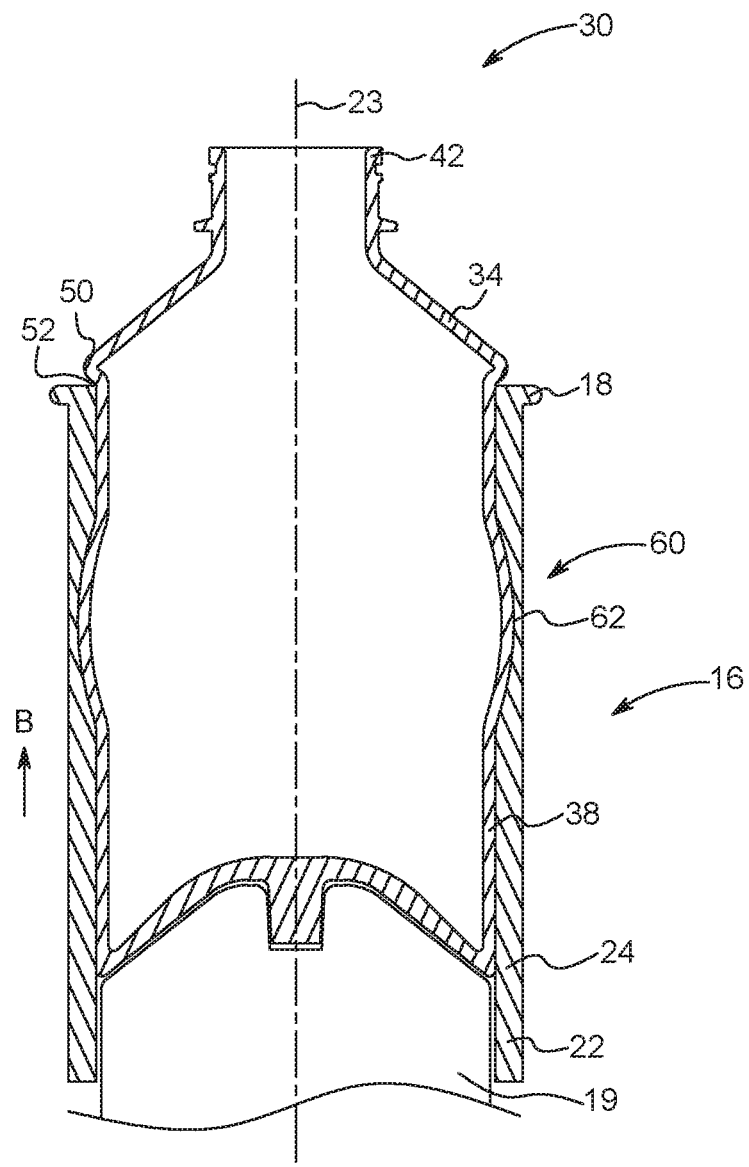
FIG. 4B is a side cross-sectional view of the pressure jacket and syringe shown in FIG. 4A, wherein the syringe retaining element is in an engaged state or position.
Figure 4C:
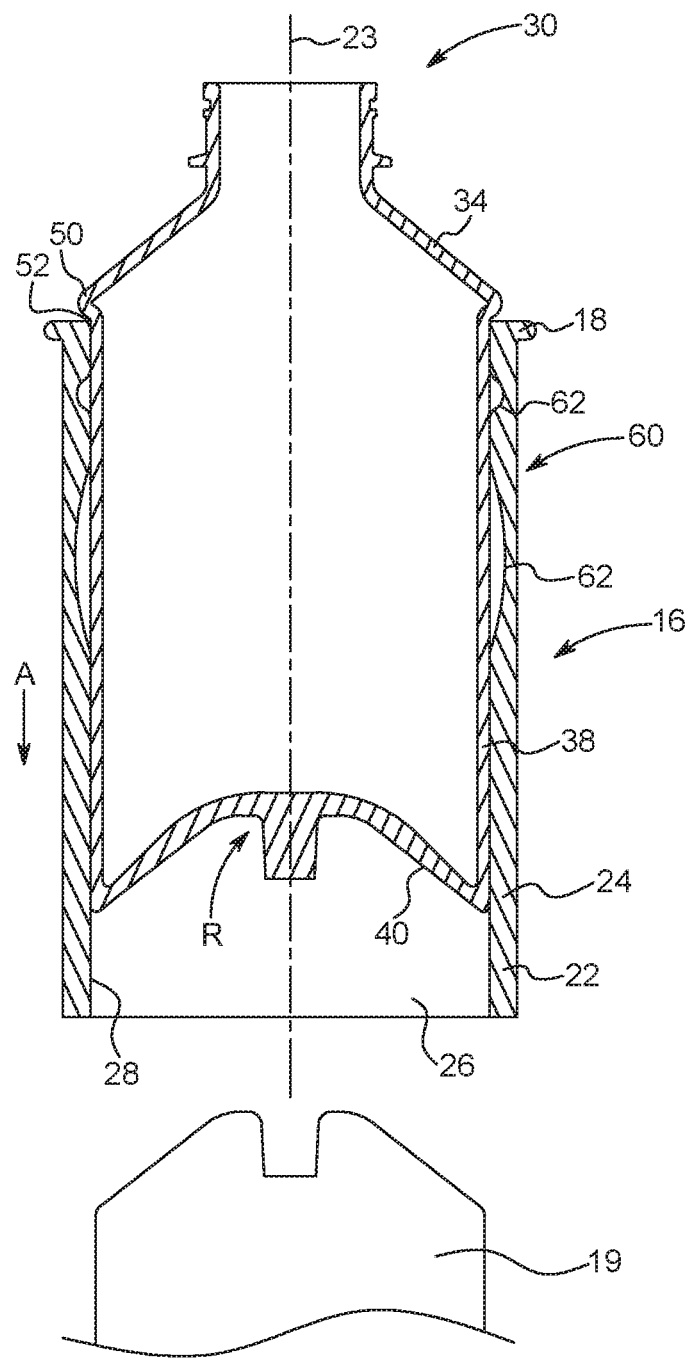
FIG. 4C is a side cross-sectional view of a syringe and a pressure jacket having a syringe retaining element in accordance with another example of the present disclosure.

With continued reference to FIGS. 4A-4B, the proximal end 36 of the syringe 30 connects to the closed end wall 40, and the distal end 34 of the syringe 30 defines a discharge neck 42 opposite the closed end wall 40. The distal end 34 may have a frusto-conical shape that gradually narrows from the sidewall 38 to the discharge neck 42. The closed end wall 40 may be shaped to interface directly with the piston 19 of the fluid injector 10 (shown in FIG. 1). For example, the closed end wall 40 may define a receiving end pocket R for interfacing directly with a similarly-shaped piston 19, which may be shaped to substantially match the shape of the closed end wall 40. The sidewall 38 and/or the end wall 40 may have uniform or non-uniform thickness. For example, the sidewall 38 may have increased thickness at the distal end 34 compared to the end wall 40. In other embodiments, the end wall 40 may have a non-uniform thickness across the receiving end pocket R.

The sidewall 38 of the syringe 30 defines a soft, pliable or flexible, yet self-supporting body that is configured to roll upon itself under the action of the piston 19. In particular, the sidewall 38 of the syringe 30 is configured to roll such that its outer surface is folded and inverted in a radially inward direction as the piston 19 is moved in a distal direction, and unroll and unfold in the opposite manner in a radially outward direction as the piston 19 is retracted in a proximal direction.

Figure 3:
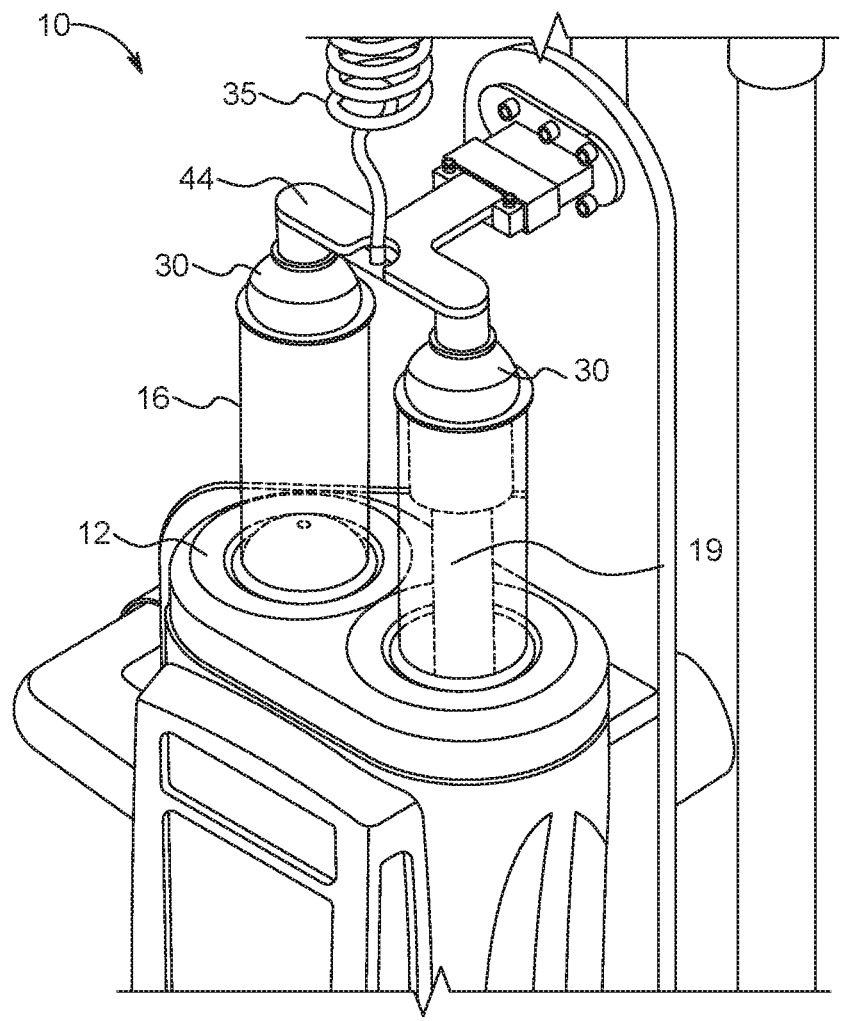
FIG. 3 is a detailed perspective view of the syringes and pressure jackets shown in FIG. 2.

With reference to FIG. 3, the distal end 34 of each syringe 30 may be optionally retained by a holding bracket 44 connected to the injector housing 14 or other retaining mechanism that prevents axial movement of the syringe 30 relative to the pressure jacket 16 during an injection procedure. The optional holding bracket 44 is movable between a first, closed position (FIG. 3) and a second, open position (FIG. 1). In the closed position, the holding bracket 44 engages the distal end 34 of the syringes 30 to retain each syringe 30 axially relative to the pressure jacket 16 and prevent or restrain movement of each syringe 30 in an axial direction relative to the pressure jacket 16 during an injection procedure. In the open position, the holding bracket 44 is moved away from engaging the distal end 34 of the syringe 30 to allow the syringe 30 to be inserted into or removed from the pressure jacket 16.

With reference to FIGS. 4A-4B, according to certain embodiments, the syringe 30 may have at least one radial flange 50 or other protruding feature protruding radially outward relative to the sidewall 38. In some examples, the at least one radial flange 50 may protrude radially outward relative to the sidewall 38 at the distal end 34 adjacent the discharge neck 42. The at least one radial flange 50 may be formed integrally with the sidewall 38 as a radial protrusion in the sidewall 38. In other examples, the at least one radial flange 50 may be formed as a separate component that is removably or non-removably attached to an outer surface of the syringe 30. For example, the at least one radial flange 50 may be attached by an adhesive, via an interference fit, or any other type of mechanical connection that secures the at least one radial flange 50 to at least a portion of an outer surface of the syringe 30 and prevents axial movement of the at least one radial flange 50 relative to the syringe 30. The at least one radial flange 50 has a diameter D3 (shown in FIG. 4A) that is larger than the inner diameter D1 of the throughbore 26 of the pressure jacket 16. In this manner, the at least one radial flange 50 limits how much of the body of the syringe 30 can be inserted into the pressure jacket 16. The at least one radial flange 50 has a proximal surface 52 that is configured to contact the distal end 18 of the pressure jacket 16. When the proximal surface 52 of the at least one radial flange 50 engages the distal end 18 of the pressure jacket 16, the syringe 30 cannot be inserted any further into the throughbore 26 of the pressure jacket 16. In certain embodiments, the distal end 18 of the pressure jacket 16 may comprise a groove (not shown) around the interior circumference of the distal surface into which the at least one radial flange 50 may fit into, thereby substantially centering the syringe 30 within the pressure jacket 16. Alternatively, the at least one radial flange 50 may be located on the discharge neck 42 of the syringe 30 (see e.g., FIGS. 5B and 5C) and may engage a feature on the injector 14 to maintain the syringe 30 within the pressure jacket 16 during a syringe filling or delivery process.

In various examples, the at least one radial flange 50 may be circumferentially continuous around an outer circumference of the sidewall 38 of the syringe 30. In other examples, the at least one radial flange 50 may be discontinuous in a circumferential direction around the outer circumference of the sidewall 38 of the syringe 30. For example, the at least one radial flange 50 may be formed from a plurality of segments circumferentially spaced apart from each other around the outer circumference of the sidewall 38. The segments of the at least one radial flange 50 may be spaced apart from each other at equal or unequal radial intervals. The segments of the at least one radial flange 50 may have equal or unequal diameters. In some examples, two or more radial flanges 50 may be axially spaced apart from one another. The radial flanges 50 may have equal or unequal diameters.

In use, the at least one radial flange 50 is configured to prevent axial movement of the syringe 30 in a proximal direction when the syringe 30 is being filled with fluid. During such procedure according to an embodiment with a rolling diaphragm-type syringe in the compressed configuration (see, e.g., FIG. 12B), the piston 19 (shown in FIG. 1) releasably engages the end wall 40 and pulls the end wall 40 of the syringe 30 in a proximal direction, as indicated by arrow A in FIGS. 4A and 4C, for example, with a force between 10 to 300 lbs. The at least one radial flange 50 restrains the distal end 34 of the syringe 30 from moving in the proximal direction due to engagement of the proximal surface 52 of the at least one radial flange 50 with a distally-facing surface of the distal end 18 of the pressure jacket 16 or with a feature on injector 14. In this manner, movement of the syringe 30 in the proximal direction relative to the pressure jacket 16 can be prevented. In addition, the at least one radial flange 50 prevents the syringe 30 from falling into the throughbore 26 of the pressure jacket 16 during loading.

With continued reference to FIGS. 4A-4D, the pressure jacket 16 may have at least one syringe retaining element 60. The at least one syringe retaining element 60 may be recessed radially outward into the interior surface 28 of the sidewall 24 of pressure jacket 16 to define at least one expansion pocket 62. The volume of the at least one expansion pocket 62 is desirably selected such that the syringe sidewall 38 can be expanded into the expansion pocket 62 during an injection procedure to provide a sufficient axial restraining force that restrains the movement of the syringe 30 relative to the pressure jacket 16 during a pressurized fluid delivery process. However, the volume of the at least one expansion pocket 62 is desirably minimized to avoid plastic yield of the syringe sidewall 38 due to excessive expansion of the syringe sidewall during injections that exceed a predetermined threshold, such as about 100 psi. As used herein, "plastic yield" means a permanent deformation of a plastic sidewall of the syringe. Plastic yield of the syringe sidewall 38 due to pressurized expansion may make it difficult to remove the radially deformed syringe from the pressure jacket 16 after an injection process.

The at least one expansion pocket 62 may be formed integrally with the interior surface 28 of the sidewall 24 of pressure jacket 16. The at least one expansion pocket 62 has an inner diameter D4 that is larger than the inner diameter D1 of the sidewall 24 of pressure jacket 16. In some examples, the at least one expansion pocket 62 may be formed as one or more through holes that extend at least partially through the sidewall 24 of the pressure jacket 16. In other examples, the at least one syringe retaining element 60 may be one or more protrusions that protrude radially inward from the interior surface 28 of the sidewall 24 of pressure jacket 16. The one or more protrusions may be dimensioned to allow insertion of the syringe 30 into the throughbore 26 during loading, but provide sufficient axial restraining force when the syringe sidewall 38 is expanded against the sidewall 24 of pressure jacket 16 under pressure during an injection procedure to help retain the syringe 30 within the pressure jacket 16. In some examples, the one or more protrusions that define the at least one syringe retaining element 60 may be integrally formed with the pressure jacket 16, or be removably or non-removably connected to the pressure jacket 16 as a separate component. In some examples, the at least one syringe retaining element 60 may have various combinations of one or more of the one or more expansion pockets 62 and one or more protrusions.

In various examples, the at least one expansion pocket 62 and/or one or more protrusions may be circumferentially continuous around a circumference of the interior surface 28 of the sidewall 24 of pressure jacket 16. In other examples, the at least one expansion pocket 62 and/or one or more protrusions may be discontinuous in a circumferential direction around the circumference of the interior surface 28 of the sidewall 24 of pressure jacket 16. For example, the at least one expansion pocket 62 and/or one or more protrusions may be formed from a plurality of segments circumferentially spaced apart from each other around the circumference of the interior surface 28 of the sidewall 24 of pressure jacket 16. The segments of the at least one expansion pocket 62 and/or one or more protrusions may be spaced apart from each other at equal or unequal radial intervals. The segments of the at least one expansion pocket 62 and/or one or more protrusions may have equal or unequal diameters. In some examples, such as shown in FIG. 4A, two or more expansion pockets 62 may be axially spaced apart from one another. The plurality of expansion pockets 62 and/or one or more protrusions may have the same or different shapes, such as a C-shape, a U-shape, or any other regular or irregular geometric shape. The plurality of expansion pockets 62 and/or one or more protrusions may have equal or unequal diameters and/or equal or unequal axial length. The plurality of expansion pockets 62 may be formed as a roughened surface on at least a portion of the interior surface 28 of the sidewall 24 of pressure jacket 16. In certain embodiments, the interior surface of the expansion pocket 62 and/or one or more protrusions may have a roughened surface. Alternatively or in combination, the exterior surface of the sidewall 38 of syringe 30 may be at least partially roughened to engage the sidewall 24 of pressure jacket 16, such as substantially at the same location of the roughened surface of the at least a portion of the interior surface 28 of the sidewall 24 of pressure jacket 16. Additionally, adjacent expansion pockets 62 and/or one or more protrusions may be separated from one another by equal or unequal axial distance. In other embodiments, the medical grade plastics of the pressure jacket 16 and the syringe 30 may be selected such that the frictional forces between the pressure jacket 16 and the syringe 30 is maximized.

In use, such as during an injection procedure where fluid is delivered from the syringe 30, the at least one expansion pocket 62 and/or one or more protrusions is configured to prevent axial movement of the syringe 30 in a distal direction when fluid is being discharged from the syringe 30. During such procedure, the piston 19 pushes the end wall 40 of the syringe 30 in a distal direction, as indicated by arrow B in FIGS. 4A-4B. As the distal end 34 of the syringe 30 is restrained from axial movement by a holding bracket 44, continued distal movement of the piston 19 builds fluid pressure within the syringe 30 (typically around 50 to 350 psi). Due to a thin and flexible construction of the sidewall 38, the sidewall 38 expands radially outward against the interior surface 28 of the sidewall 24 of pressure jacket 16. Because the at least one expansion pocket 62 is recessed relative to the interior surface 28 of the sidewall 24 of pressure jacket 16, the sidewall 38 of the syringe 30 can expand radially outward locally in the region of the at least one expansion pocket 62. As the sidewall 38 of the syringe 30 expands to fill the expansion pocket 62, the syringe 30 becomes engaged with the pressure jacket 16 by a surface-to-surface frictional contact between the sidewall 38 of the syringe 30 with the interior surface 28 of the sidewall 24 of pressure jacket 16 and the expansion pocket 62. Due to such surface-to-surface contact, the syringe 30 is prevented from moving axially in the distal direction under the proximally directed force of the piston 19. Further, as the injection pressure increases, the amount of frictional force between the sidewall 38 of the syringe 30 with the interior surface 28 of the sidewall 24 of pressure jacket 16 increases. In this manner, movement of the syringe 30 in the distal direction relative to the pressure jacket 16 can be prevented or minimized. The engagement of the syringe sidewall 38 with the expansion pocket 62 and/or one or more protrusions reduces or eliminates an axial load on the holding bracket 44. In addition, a torque load on the holding bracket 44 can be reduced or eliminated when only one syringe 30 of a two syringe injector is pressurized to deliver fluid therefrom.

The axial frictional force between the exterior wall of the syringe 30 and the interior surface 28 of the pressure jacket 16 and the at least one syringe retaining element 60 is a function of a normal force (i.e., force exerted on the exterior wall of the syringe 30 and the interior surface 28 of the pressure jacket 16 in a radial direction) and a coefficient of friction at the surface-to-surface interface between the exterior of the syringe 30 and the interior surface 28 of the pressure jacket 16, including the surface-to-surface contact between the exterior of the syringe 30 and the at least one syringe retaining element 60. This axial frictional force opposes the relative axial movement of the syringe 30 and the pressure jacket 16 during an injection procedure. The coefficient of friction is a function of the types of materials from which the pressure jacket 16, the at least one syringe retaining element 60, and the syringe 30 are made. The coefficient of friction is also a function of surface structure, such as surface roughness, of the materials from which the pressure jacket 16, the at least one syringe retaining element 60, and the syringe 30 are made. The coefficient of friction is further dependent on the presence of any fluid between the exterior of the syringe 30 and the interior surface 28 of the pressure jacket 16. Typically, any fluid between the syringe 30 and the pressure jacket 28 lowers the coefficient of friction, and thereby the overall frictional force between the syringe 30 and the pressure jacket 16.

The axial frictional force between the syringe 30 and the pressure jacket 16 may be equal to or less than an axial force on the syringe 30 during pressurized delivery of fluid from the syringe 30. As the fluid within the syringe 30 is pressurized, the syringe 30 expands or swells in a radially outward direction to engage the interior surface 28 of the pressure jacket 16 and the at least one syringe retaining element 60. With an increase in pressure, the radial force with which the syringe 30 is expanded increases, thereby increasing the normal force between the syringe 30 and the pressure jacket 16. As the normal force increases, the axial frictional force also increases based on a coefficient of friction at the surface-to-surface interface between the exterior of the syringe 30 and the interior surface 28 of the pressure jacket 16, including the surface-to-surface contact between the exterior of the syringe 30 and the at least one syringe retaining element 60.

Figure 4D:
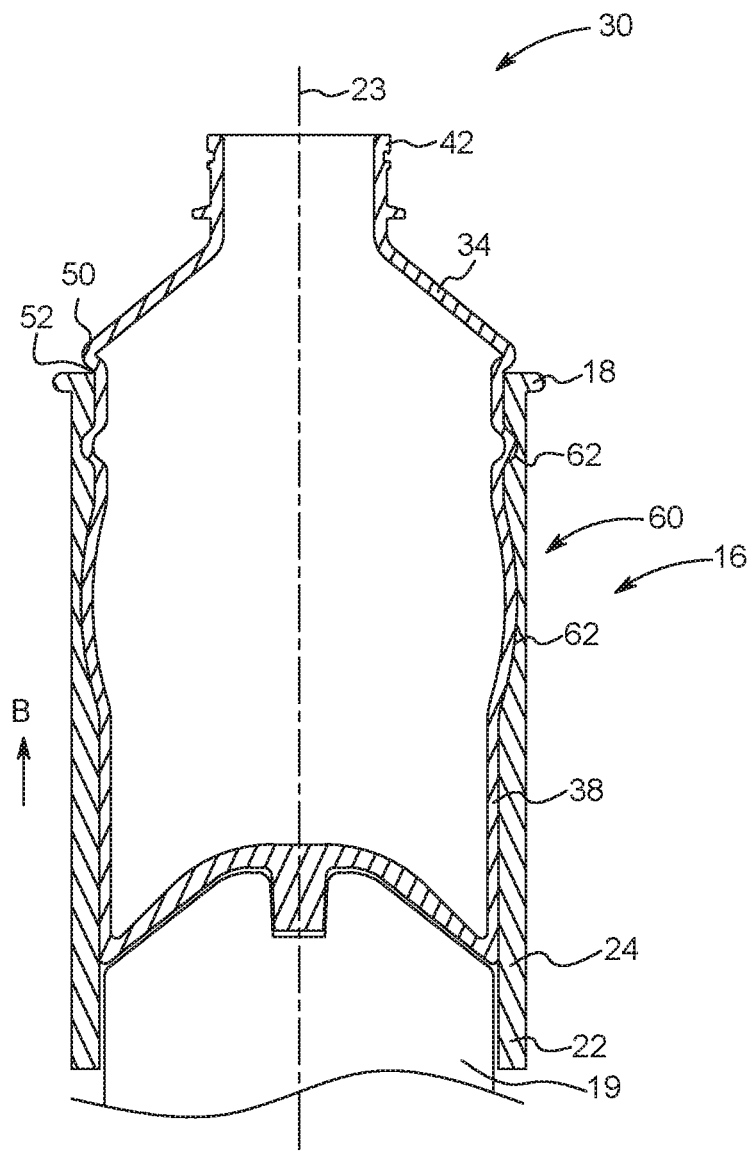
FIG. 4D is a side cross-sectional view of the pressure jacket and syringe shown in FIG. 4C, wherein the syringe retaining element is in an engaged state or position.

During a fluid delivery procedure, the piston 19 pushes the end wall 40 of the syringe 30 in a distal direction, as indicated by arrow B in FIGS. 4B and 4D. As the distal end 34 of the syringe 30 is restrained from axial movement by the holding bracket 44 (shown in FIG. 3), continued distal movement of the piston 19 builds fluid pressure within the syringe 30 (typically around 50 to 350 psi). Due to a thin and flexible construction of the sidewall 38, the sidewall 38 expands radially outward against the interior surface 28 of the pressure jacket 16. Because the at least one expansion pocket 62 is recessed relative to the interior surface 28 of the pressure jacket 16, the sidewall 38 of the syringe 30 can expand radially outward locally in the region of the at least one expansion pocket 62, as shown in FIGS. 4B and 4D. As the sidewall 38 of the syringe 30 expands to fill the expansion pocket 62, the syringe 30 becomes engaged with the pressure jacket 16 by a surface-to-surface contact between the sidewall 38 of the syringe 30 with the interior surface 28 of the throughbore 26 and the expansion pocket 62. Due to such surface-to-surface contact, the syringe 30 is prevented from moving axially in the distal direction under the proximally directed force of the piston 19. In this manner, movement of the syringe 30 in the distal direction relative to the pressure jacket 16 can be prevented. The engagement of the syringe sidewall 38 with the expansion pocket 62 reduces or eliminates an axial load on the holding bracket 44. In addition, a torque load on the holding bracket 44 can be reduced or eliminated when only one syringe 30 is pressurized to deliver fluid therefrom.

In further examples, the at least one syringe retaining element 60 may be a recess in the interior surface 28 of the sidewall 24 of pressure jacket 16 that is filled with an elastic material, such as a thermoplastic elastomer or a silicone material. The elastic material desirably fills at least a portion of the expansion pocket 62 and is sufficiently spaced apart from the syringe sidewall 38 to allow insertion of the syringe 30 into the throughbore 26. During a fluid delivery procedure, the syringe sidewall 38 expands radially outward to contact the elastic material. The elastic material itself may deform, such as by being compressed, due to contact with the syringe sidewall 38. The elastic material may have a higher coefficient of friction relative to the interior surface 28 of the sidewall 24 of pressure jacket 16. In this manner, the elastic material may "stick" to the sidewall 38 of the syringe 30, thereby reducing or eliminating axial movement of the syringe 30 during an injection procedure. In some examples, the elastic material may be provided within grooves and/or holes in the pressure jacket 16. The elastic material thus may define a deformable, resilient expansion zone into which the syringe sidewall 38 may extend. After the fluid delivery procedure, the syringe sidewall 38 reverts to its original shape, thereby decompressing the elastic material into its original shape. The syringe 30 may be removed from the throughbore 26 without interference with the elastic material. The elastic material may be permanently attached to the interior sidewall 24 of pressure jacket 16 or may be removably attached to the sidewall 24 of pressure jacket 16 such that it may be replaced after a certain time period. In other embodiments, the elastic material may be provided on the exterior surface of the sidewall 38 of the syringe 30, for example at substantially the location so that the elastic material fits within the expansion pocket 62. According to this embodiment, the diameter of the syringe 30 with the elastic material may be less than the diameter of the throughbore 26.

With reference to FIGS. 5A-15B, a pressure jacket 16 having at least one syringe retaining element 60 and a syringe 30 configured for use with the pressure jacket 16 are shown in accordance with further examples or embodiments of the present disclosure. The components of the pressure jacket 16 and the syringe 30 shown in FIGS. 5A-15B are substantially similar or identical to the pressure jacket 16 and the syringe 30 described herein with reference to FIGS. 1-4B. Reference numerals in FIGS. 5A-15B are used to illustrate identical components of the corresponding reference numerals in FIGS. 1-4B. As the previous discussion regarding the pressure jacket 16 and the syringe 30 generally shown in FIGS. 1-4B is applicable to the examples of the present disclosure shown in FIGS. SA-15B, only the relative differences between the pressure jacket 16 and the syringe 30 generally shown in FIGS. 1-4B and the pressure jacket 16 and the syringe 30 generally shown in FIGS. SA-15B are discussed herein.

Figure 5A:
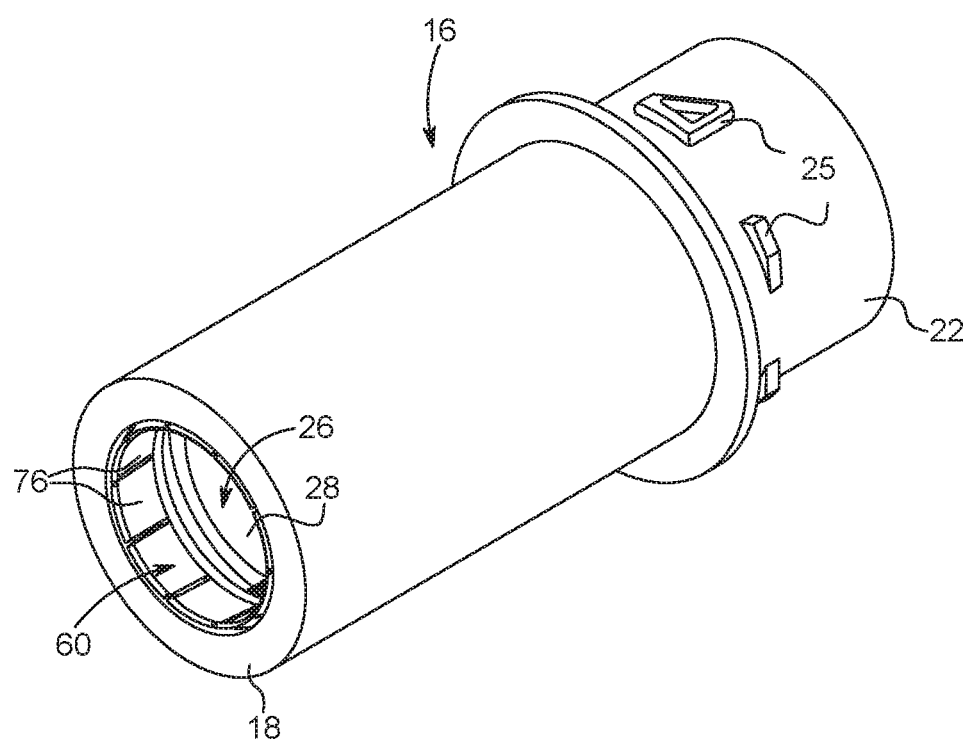
FIG. 5A is a front perspective view of a pressure jacket having a syringe retaining element in accordance with another example of the present disclosure.
Figure 5B:
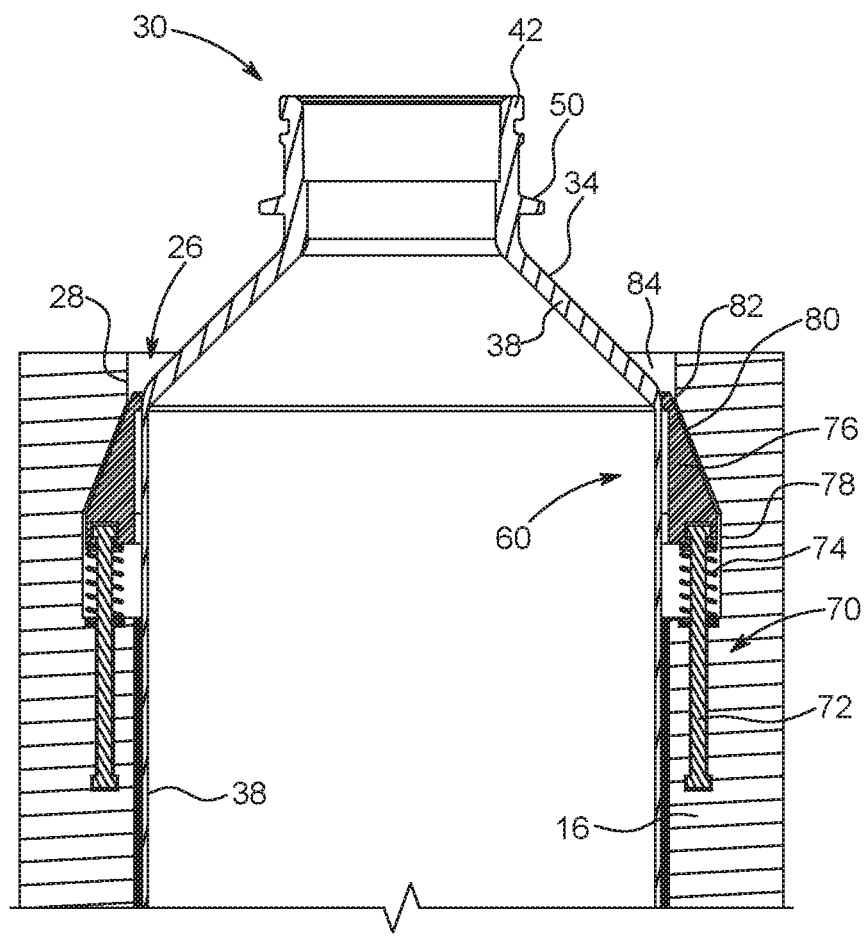
FIG. 5B is a side cross-sectional view of the pressure jacket shown in FIG. 5A in use with a syringe, wherein the syringe retaining element is in a disengaged state or position.
Figure 5C:
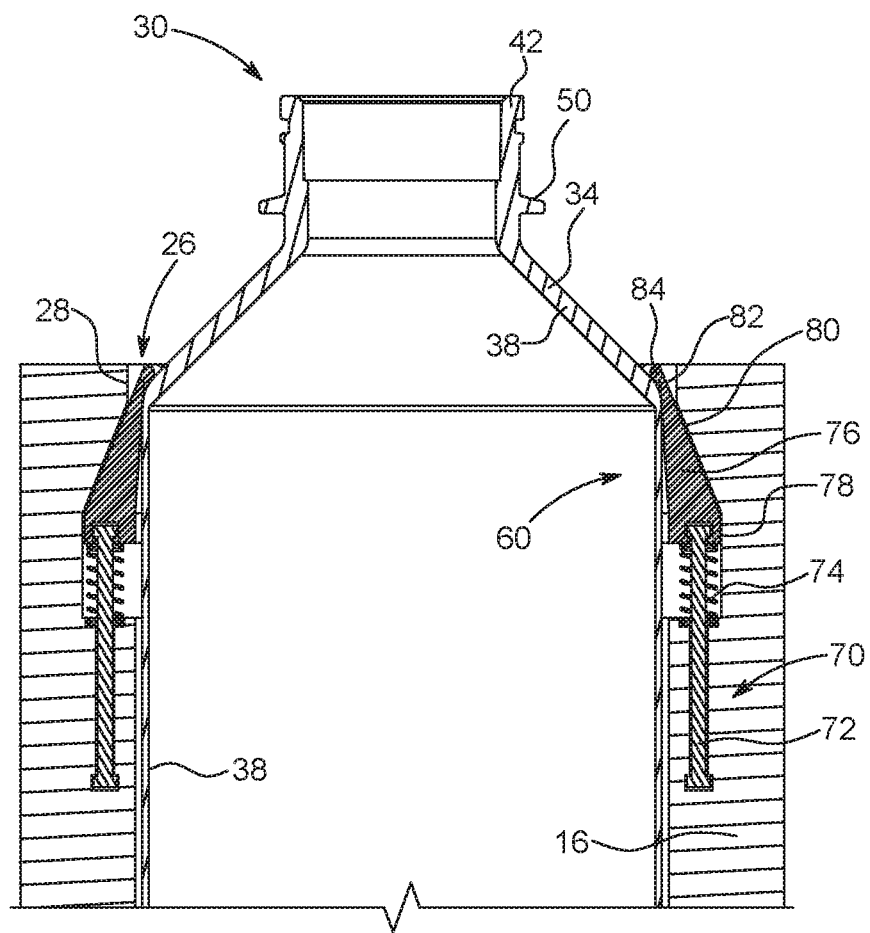
FIG. 5C is a side cross-sectional view of the pressure jacket and syringe shown in FIG. 5B, wherein the syringe retaining element is in an engaged state or position.

With reference to FIGS. 5A-5C, the pressure jacket 16 has at least one syringe retaining element 60 that is configured for movement between a disengaged position or state (FIG. 5B) and an engaged position or state (FIG. 5C) due to movement of an actuation mechanism 70 (shown in FIGS. 5B-5C). In various examples, the actuation mechanism 70 may be a mechanical mechanism, an electrical mechanism, an electromechanical mechanism, a pneumatic mechanism, a hydraulic mechanism, or a combination of any of these mechanisms. In some examples, the actuation mechanism 70 may be a rod 72 (shown in FIGS. 5B-5C) that is movable axially relative to the pressure jacket 16. The rod 72 may be movable axially relative to the pressure jacket 16 by a solenoid or a mechanical linkage arrangement operatively connected to the piston 19 (shown in FIGS. 4A-4B). In some examples, the rod 72 may be connected to an electrically activated component, such as a nitinol wire or an electroactive polymer. The rod 72 may be biased to the disengaged position or the engaged position by a biasing member 74. In some examples, the rod 72 is biased to the engaged position by a biasing member 74 that is configured as a spring.

With continued reference to FIGS. SA-5C, the at least one syringe retaining element 60 has a plurality of radially extendable and retractable fingers 76 (hereinafter "retractable fingers 76") arranged circumferentially within a pocket 78 extending radially outward into the interior surface 28 of the pressure jacket 16. The plurality of retractable fingers 76 may be circumferentially continuous around a circumference of the interior surface 28 of the distal portion of the sidewall 24 of pressure jacket 16. In other examples, the retractable fingers 76 may be discontinuous in a circumferential direction around the circumference of the interior surface 28 of the distal portion of the sidewall 24 of pressure jacket 16. For example, the retractable fingers 76 may be formed from a plurality of segments circumferentially spaced apart from each other around the circumference of the interior surface 28 of the distal portion of the sidewall 24 of pressure jacket 16. The segments of the at least one syringe retaining element 60 may be spaced apart from each other at equal or unequal radial intervals.

Each of the plurality of retractable fingers 76 is operatively connected with the actuation mechanism 70 such that movement of the actuation mechanism 70 between the disengaged position or state and the engaged position or state also moves the at least some of the plurality of retractable fingers 76 between a disengaged position (FIG. 5B) and an engaged position (FIG. 5C). In some examples, each retractable finger 76 may be connected to at least a portion of a respective rod 72. The biasing member 74 may be arranged between a proximal end of at least one of the retractable fingers 76 and a distal end of the pocket 78.

With continued reference to FIGS. 5B-5C, the pocket 78 has a first inclined surface 80 at its distal end that guides the movement of the retractable fingers 76 between the disengaged position and the engaged position. The first inclined surface 80 may be configured to guide the retractable fingers 76 both distally and radially inward relative to the pressure jacket 16. In some examples, the retractable fingers 76 may have a second inclined surface 82 that corresponds to the first inclined surface 80 of the pocket 78. In use, the second inclined surface 82 of the retractable fingers 76 is configured to slide along the first inclined surface 80 of the pocket 78 such that the retractable fingers 78 are moved both distally and radially inward from the disengaged position (FIG. 5B) and the engaged position (FIG. 5C).

With continued reference to FIGS. 5B-5C, a distal end of the retractable fingers 76 has a radially inwardly-protruding retaining lip 84 that is configured to engage at least a portion of the frusto-conical distal end 34 of the syringe 30 when the retractable fingers 76 are positioned in the engaged position (FIG. 5C). In the engaged position, at least a portion of the retractable fingers 76 is configured to be extended radially inward into the throughbore 26 of the pressure jacket 16 to contact at least a portion of the sidewall 38 of the syringe 30. During an injection procedure, radial expansion of the syringe 30 increases a contacting force between the sidewall 38 of the syringe 30 and the retractable fingers 76 to prevent or limit axial movement of the syringe 30 relative to the pressure jacket 16. Such axial movement of the syringe 30 is further limited or prevented by interaction of the retaining lip 84 with the distal end 34 of the syringe 30. In some examples, the retractable fingers 76 may be configured to reduce or eliminate the axial force exerted by the syringe 30 on the holding bracket 44 during an injection procedure. In examples where the retractable fingers 76 are configured to eliminate the axial force exerted by the syringe 30 on the holding bracket 44, the holding bracket 44 need not be provided, or the holding bracket 44 may be used as a supplemental measure for axial retention of the syringe 30 within the pressure jacket 16, for example to hold the syringe 30 within the pressure jacket 16 prior to the injection procedure.

Figure 6A:
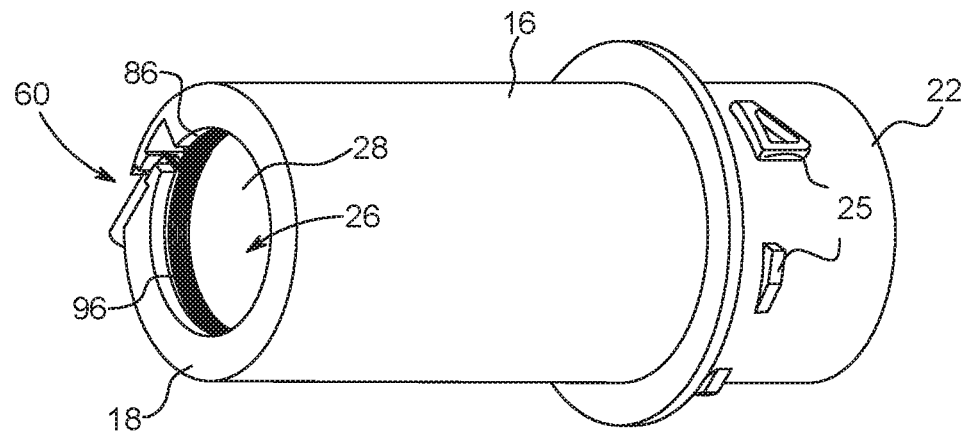
FIG. 6A is a front perspective view of a pressure jacket having a syringe retaining element in accordance with another example of the present disclosure.
Figure 6B:
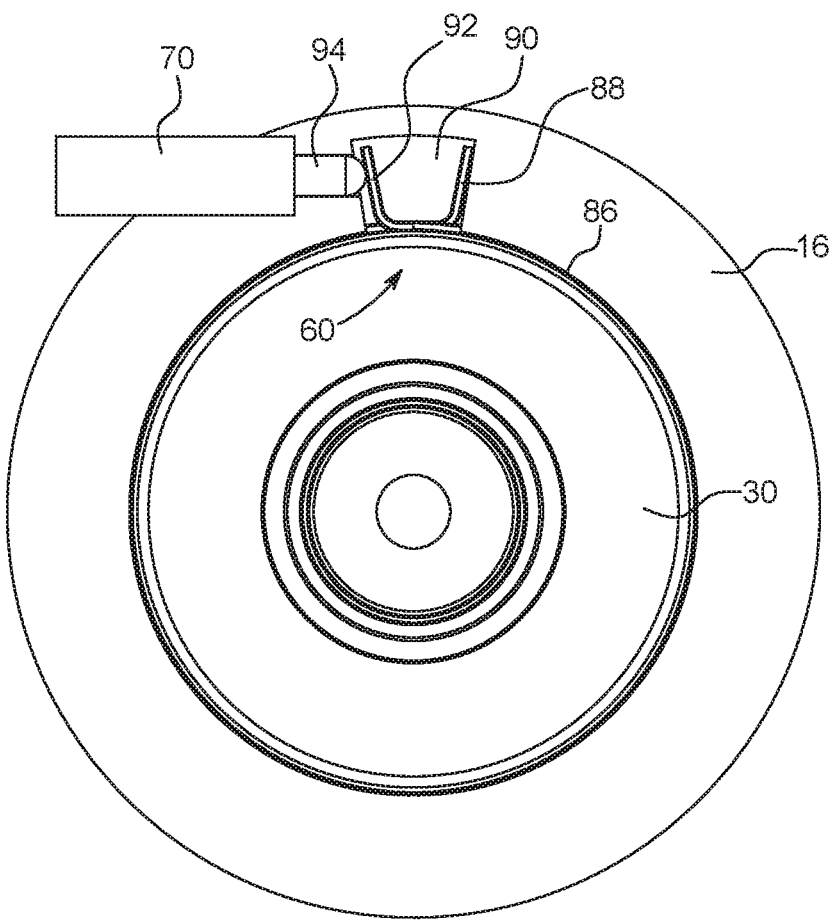
FIG. 6B is a top view of the pressure jacket and the syringe retaining element shown in FIG. 6A.
Figure 6C:
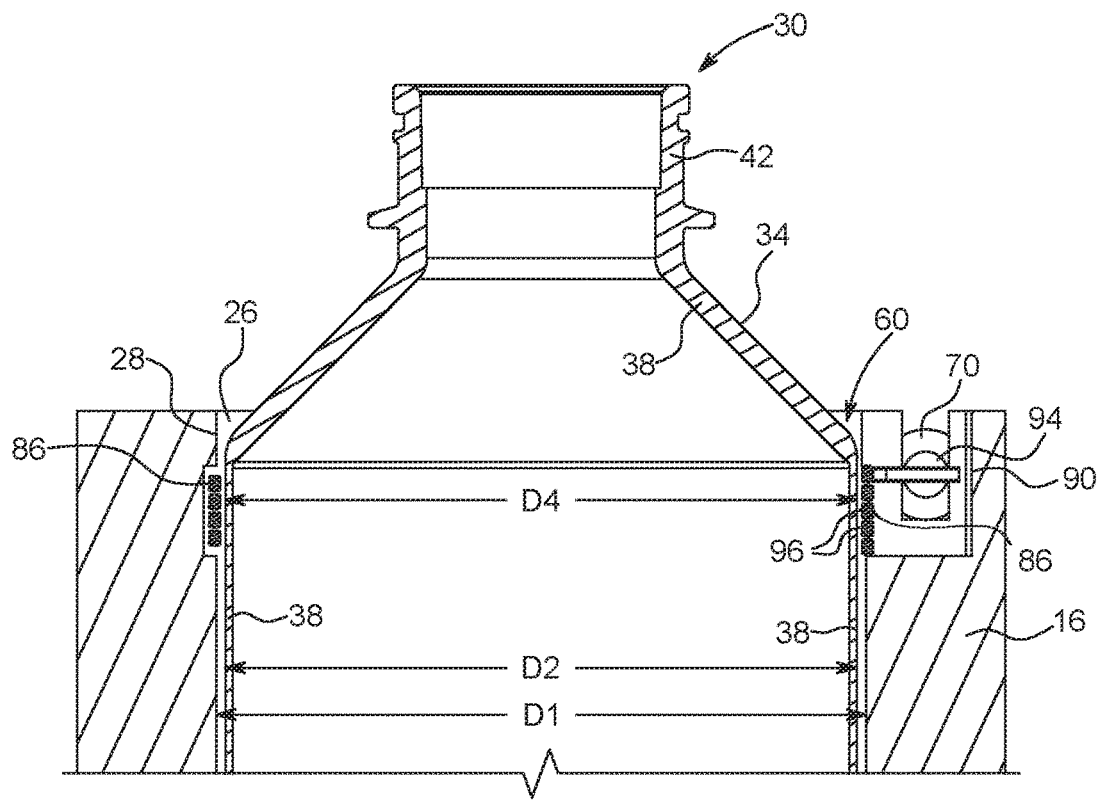
FIG. 6C is a side cross-sectional view of the pressure jacket shown in FIG. 6A in use with a syringe, wherein the syringe retaining element is in a disengaged state or position.
Figure 6D:
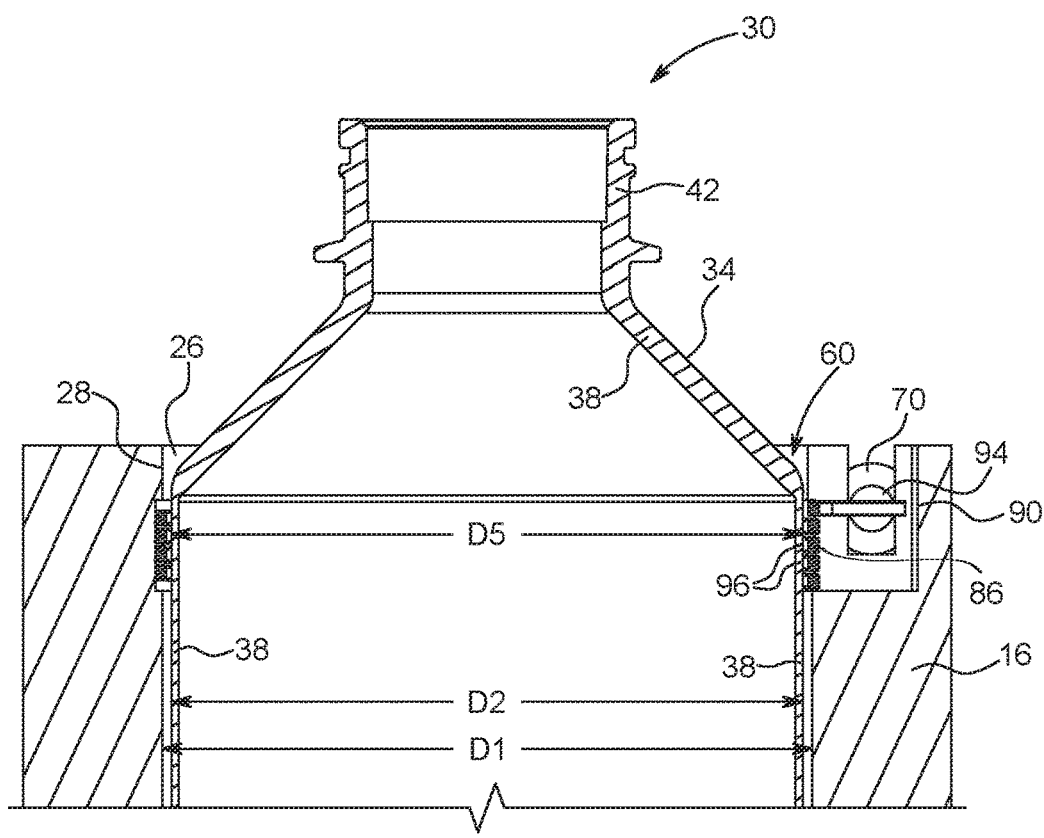
FIG. 6D is a side cross-sectional view of the pressure jacket and syringe shown in FIG. 6B, wherein the syringe retaining element is in an engaged state or position.

With reference to FIGS. 6A-6D, the pressure jacket 16 has at least one syringe retaining element 60 that is configured for movement between a disengaged position or state (FIG. 6C) and an engaged position or state (FIG. 6D) due to movement of an actuation mechanism 70 (shown in FIG. 6B). With reference to FIG. 6B, the actuation mechanism 70 may have a linearly movable dowel 94 configured for contacting at least a portion of a spring 86 that is movable between a disengaged position or state and an engaged position or state with movement of the dowel 94. In some examples, a first end 88 of the spring 86 is engaged with a pocket 90 extending radially outward into the interior surface 28 (shown in FIG. 6A) of the pressure jacket 16. A second end 92 of the spring 86 is operatively connected with at least a portion of the actuation mechanism 70, such as a linearly movable dowel 94. The spring 86 is wound in a plurality of coils 96 (shown in FIGS. 6C-6D) axially spaced apart from one another.

The spring 86 may be biased to the engaged position. In the engaged position, the coils 96 have a first diameter D4 that is smaller than the inner diameter D1 of the throughbore 26 and the outer diameter D2 of the syringe 30 such that the coils 96 of the spring 86 contact the sidewall 38 of the syringe 30. During an injection procedure, radial expansion of the syringe 30 increases a contacting force between the sidewall 38 of the syringe 30 and the coils 96 of the spring 86 to prevent or limit axial movement of the syringe 30 relative to the pressure jacket 16. Alternatively, the spring 86 may be biased to the disengaged position and the actuation mechanism 70 may move the spring into the engaged position.

To move the spring 86 from the engaged position to the disengaged position, the dowel 94 is operated to move the second end 92 of the spring 86 toward the first end 88, thereby spreading the coils 96 of the spring 86 radially apart. In the disengaged position, the coils 96 have a second diameter D5 that is larger than or equal to the inner diameter D1 of the throughbore 26 and larger than the outer diameter D2 of the syringe 30 to allow a free insertion or removal of the syringe 30 from the throughbore 26 of the pressure jacket 16. Other actuation mechanisms which move the spring 86 between the disengaged position and the engaged position, such as lever or a clamping mechanism to move the first end 88 and the second end 92 together and apart are also contemplated.

Figure 7A:
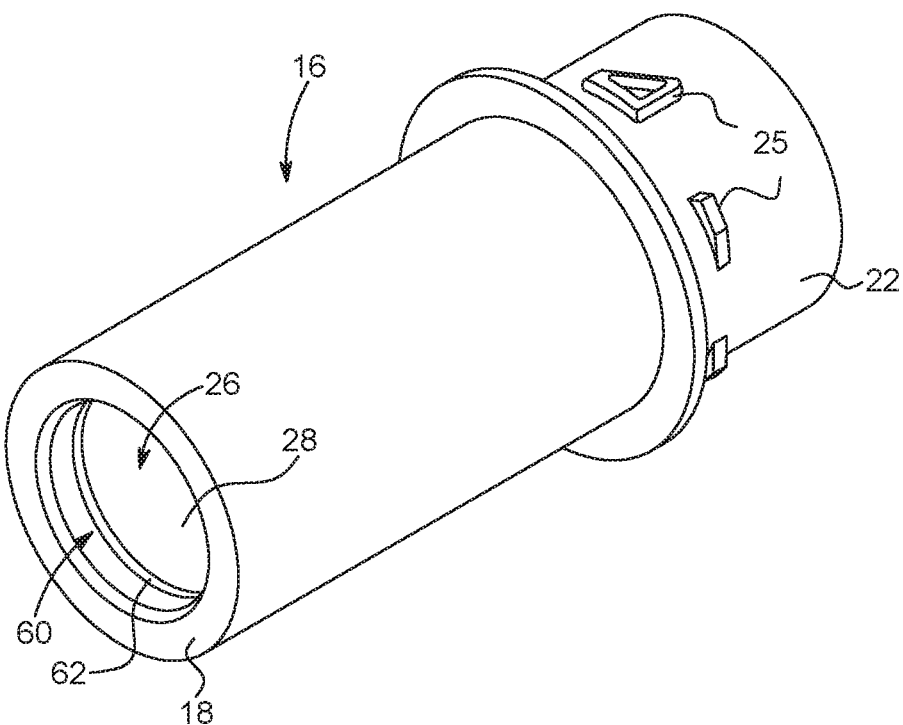
FIG. 7A is a front perspective view of a pressure jacket having a syringe retaining element in accordance with another example of the present disclosure.

With reference to FIG. 7A, the pressure jacket 16 may have at least one syringe retaining element 60 that is recessed radially outward into the interior surface 28 of the sidewall 24 of pressure jacket 16 to define at least one expansion pocket 62. The at least one expansion pocket 62 has an inner diameter that is larger than the inner diameter of the throughbore 26. In some examples, the expansion pocket 62 may be circumferentially continuous around a circumference of the interior surface 28 of the throughbore 26. In other examples, the expansion pocket 62 may be discontinuous in a circumferential direction around the circumference of the interior surface 28 of the throughbore 26. For example, the expansion pocket 62 may be formed from a plurality of segments circumferentially spaced apart from each other around the circumference of the interior surface 28 of the throughbore 26. The segments of the expansion pocket 62 may be spaced apart from each other at equal or unequal radial intervals. In some examples, two or more expansion pockets 62 may be axially spaced apart from one another.

Figure 7B:
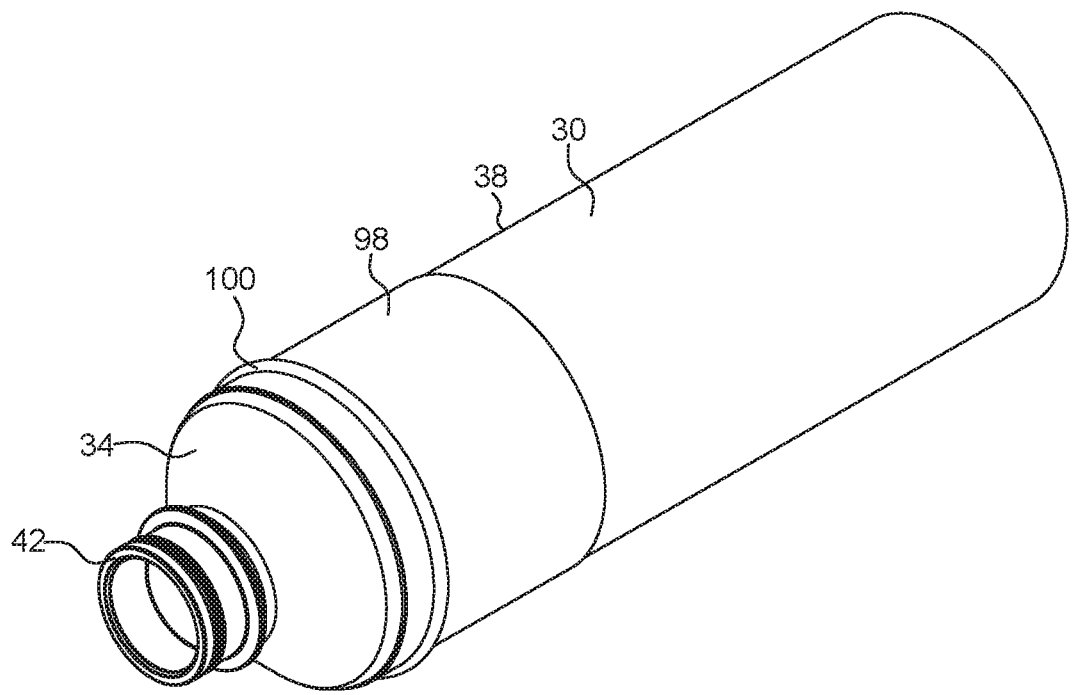
FIG. 7B is a front perspective view of a syringe for use with the pressure jacket shown in FIG. 7A.

With reference to FIG. 7B, the syringe 30 may have at least one label 98 extending around at least a portion of an exterior side of the sidewall 38. In some examples, an axial position of the at least one label 98 relative to the syringe 30 is fixed. For example, the at least one label 98 may be adhesively affixed to the syringe 30, or it may be tightly bound around the outer part of the sidewall 38. The label 98 may be made of a material that increases frictional forces between the sidewall 38 of the syringe 30 and the sidewall 24 of pressure jacket 16, when the label 98 is held between the wall 38 of the syringe 30 and the sidewall 24 of pressure jacket 16 when the syringe 30 is pressurized and radially expanded during an injection protocol.

With continued reference to FIG. 7B, the at least one label 98 may have one or more protrusions 100 that protrude radially outward relative to the syringe 30 and a body 102 of the at least one label 98. Alternatively or in addition, the sidewall 38 of the syringe 30 may have one or more protrusions, as described herein, that engage the at least one expansion pocket 62. In some examples, the protrusion 100 may be circumferentially continuous around a circumference of the outer surface of the label 98. In other examples, the protrusion 100 may be discontinuous in a circumferential direction around the circumference of the outer surface of the label 98. For example, the protrusion 100 may be formed from a plurality of segments circumferentially spaced apart from each other around the circumference of the outer surface of the label 98. The segments of the protrusion 100 may be spaced apart from each other at equal or unequal radial intervals. In some examples, two or more protrusions 100 may be axially spaced apart from one another.

Figure 7C:
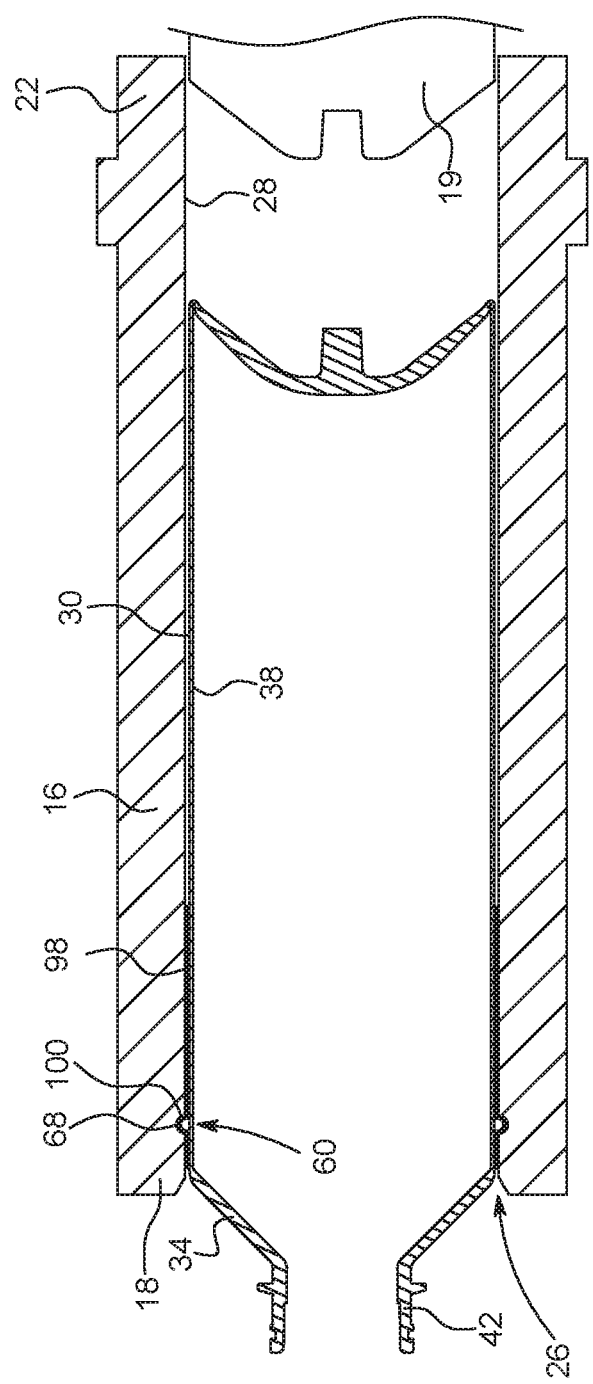
FIG. 7C is a side cross-sectional view of the pressure jacket and syringe of FIGS. 7A-7B showing the syringe retained within the pressure jacket.
Figure 7D:
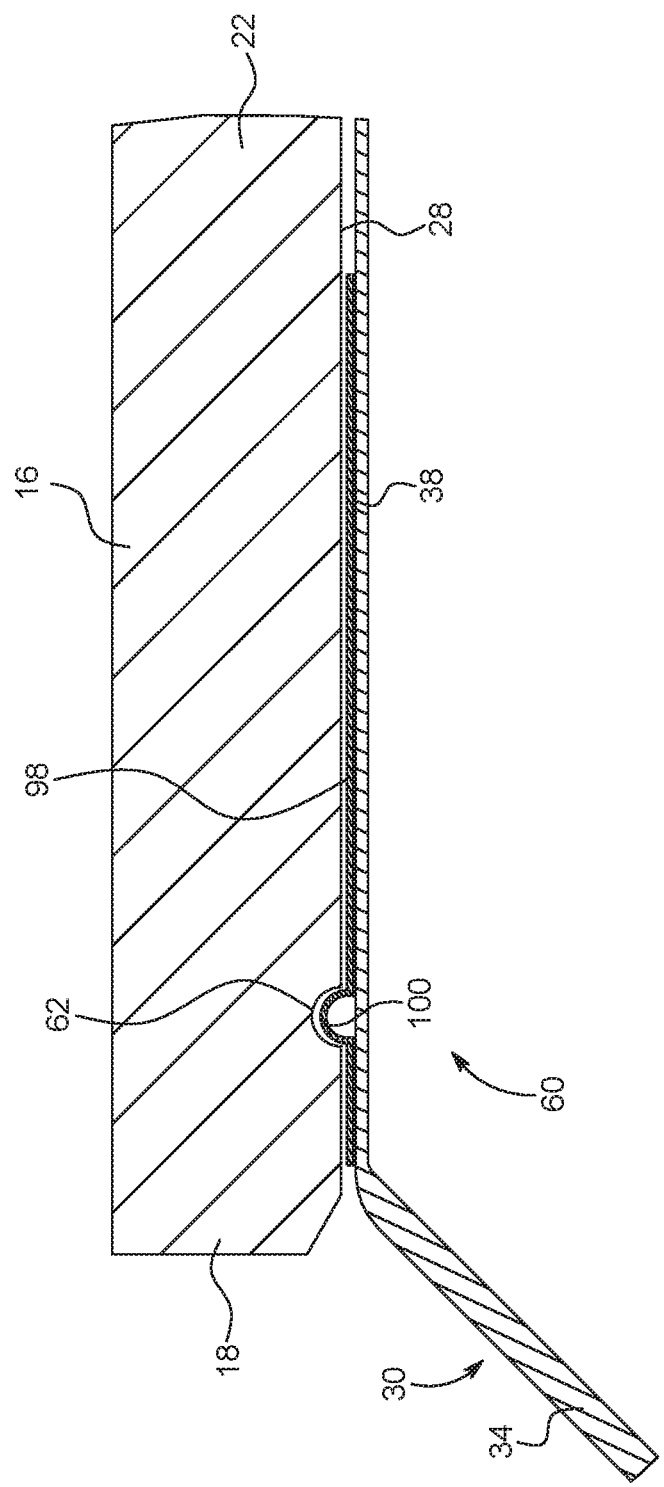
FIG. 7D is a detailed side cross-sectional view of the pressure jacket and syringe of FIG. 7C.

With reference to FIGS. 7C-7D, the one or more protrusions 100 on the label 98 are configured to interact with the at least one expansion pocket 62 of the pressure jacket 16. When the syringe 30 is inserted into the pressure jacket 16, the label 98 is interposed between an outer surface of the syringe 30 and an interior surface 28 of the sidewall 24 of the pressure jacket 16. The one or more protrusions 100 are desirably positioned such that its axial position corresponds to an axial position of the at least one expansion pocket 62 on the pressure jacket 16. The one or more protrusions 100 may be configured to expand into the at least one expansion pocket 62 when the syringe 30 is pressurized. When the syringe 30 is not pressurized, the one or more protrusions 100 are not forcibly held within the at least one expansion pocket 62 to allow the syringe 30 to be inserted into or removed from the pressure jacket 16.

In use, such as during an injection procedure where fluid is delivered from the syringe 30, the protrusion 100 is configured to prevent axial movement of the syringe 30 in a distal direction when fluid is being discharged from the syringe 30. As the sidewall 38 of the syringe 30 expands radially outward under pressure, the protrusion 100 on the label 98 moves radially outward with movement of the sidewall 38 to engage with the expansion pocket 62. In this manner, the label 98 becomes engaged with the pressure jacket 16 by a surface-to-surface contact between the protrusion 100 with the expansion pocket 62 and between the body 102 of the label 98 with the interior surface 28 of the sidewall 24 of the pressure jacket 16. Due to such surface-to-surface contact, the label 98, and thereby the syringe 30, is prevented from moving axially in the distal direction under the proximally directed force of the piston 19. In this manner, movement of the syringe 30 in the distal direction relative to the pressure jacket 16 can be prevented.

Figure 8A:
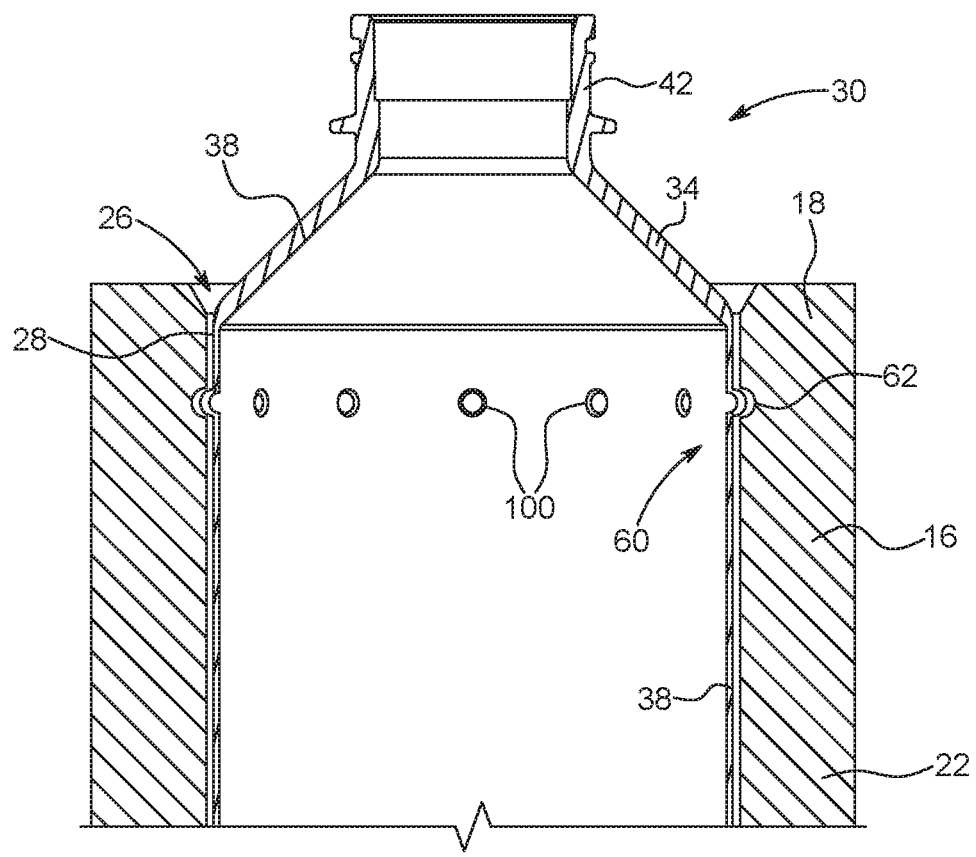
FIG. 8A is a side cross-sectional view of a pressure jacket having a syringe retaining element and a syringe configured for use therewith in accordance with another example of the present disclosure.
Figure 8B:
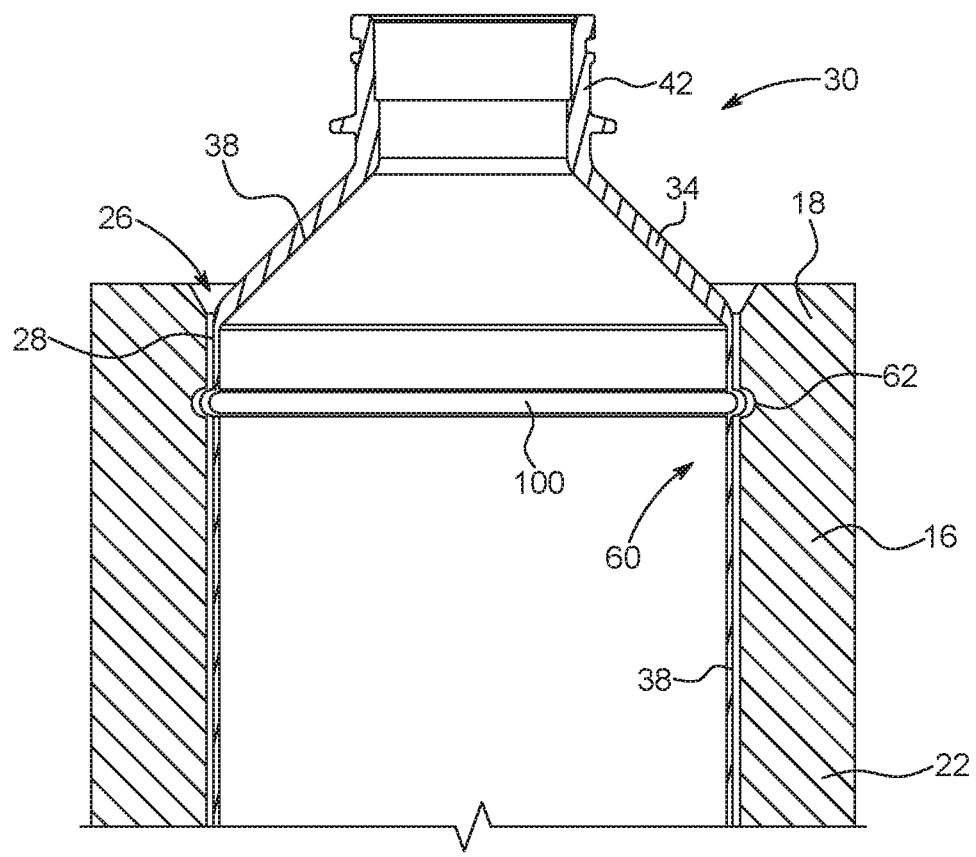
FIG. 8B is a side cross-sectional view of a pressure jacket having a syringe retaining element and a syringe configured for use therewith in accordance with another example of the present disclosure.
Figure 8C:
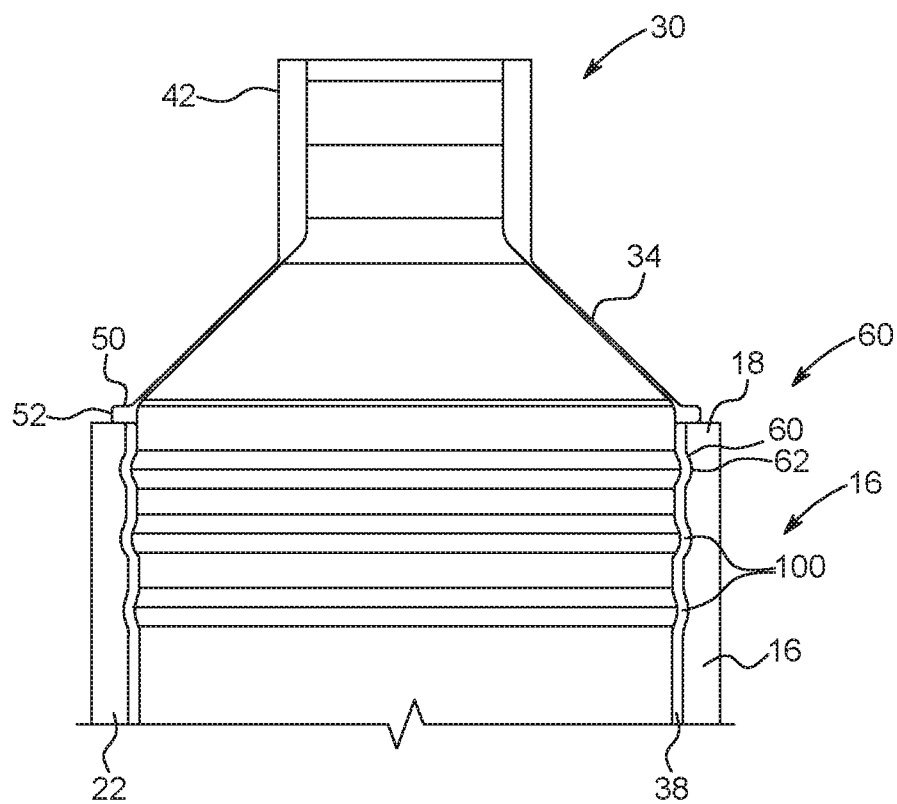
FIG. 8C is a side cross-sectional view of a pressure jacket having a syringe retaining element and a syringe configured for use therewith in accordance with another example of the present disclosure.

With reference to FIGS. 8A-8C, the pressure jacket 16 may have at least one syringe retaining element 60 in the form of an expansion pocket 62. The expansion pocket 62 may be substantially similar or identical to the expansion pocket 62 described herein with reference to FIGS. 4A-4B and FIGS. 7C-7D. Instead of the one or more protrusions 100 being formed on the label 98 affixed to the syringe 30, such as described herein with reference to FIGS. 7A-7D, the syringes 30 of FIGS. 8A-8C may have the one or more protrusions 100 as an integral part of the sidewall 38 of the syringe 30.

With reference to FIG. 8A, the one or more protrusions 100 protrude radially outward relative to the outer surface of the syringe 30. The one or more protrusions 100 may be formed as a plurality of individual protrusions 100 that are discontinuous in a circumferential direction around the circumference of the outer surface of the label 98. For example, the one or more protrusions 100 may be formed as a plurality of segments circumferentially spaced apart from each other around the circumference of the outer surface of the syringe 30. The one or more protrusions 100 may be spaced apart from each other at equal or unequal radial intervals. In some examples, two or more rows of protrusions 100 may be axially spaced apart from one another. Each of the protrusions 100 may have an identical or different shape relative to the other protrusions 100. In some examples, the protrusions 100 may have a semi-spherical shape. In other examples, the protrusions may have a semi-ovoidal or semi-ellipsoidal shape. The one or more protrusions 100 on the syringe 30 may be configured to align with and interact with the at least one expansion pocket 62 of the pressure jacket 16. In some examples, the expansion pocket 62 may be formed a circumferentially continuous ring around the inner circumference of the pressure jacket 16. In other examples, the at least one expansion pocket 62 may be a plurality of expansion pockets 62 that corresponds to the plurality of protrusions 100. Each of the plurality of expansion pockets 62 may be configured to receive at least one of the one or more protrusions 100. The one or more protrusions 100 are desirably positioned such that their axial position corresponds to an axial position of the at least one expansion pocket 62 on the pressure jacket 16. The one or more protrusions 100 are configured to expand into the at least one expansion pocket 62 when the syringe 30 is pressurized. When the syringe 30 is not pressurized, the projections 100 are not substantially positioned within the expansion pocket 62 to allow the syringe 30 to be inserted into or removed from the pressure jacket 16. In certain embodiments, when the syringe 30 is not pressurized, the projections 100 are slightly positioned within the expansion pocket 62 to allow the syringe 30 to "click" into place when inserted into pressure jacket 16 and be retained at the proper position, and may allow syringe 30 to be readily removed from pressure jacket 16 upon completion of an injection protocol.

With reference to FIGS. 8B-8C, the one or more protrusions 100 are circumferentially continuous around a circumference of the outer surface of the syringe 30. Similar to the interaction between the one or more protrusions 100 with the at least one expansion pocket 62 described herein with reference to FIG. 8A, the one or more protrusions 100 in FIGS. 8B-8C are configured to interact with the at least one expansion pocket 62 of the pressure jacket 16. A single protrusion 100 on the syringe 30 may be configured for interacting with a single expansion pocket 62 on the pressure jacket 16 (FIG. 8B), or a plurality of axially offset protrusions 100 on the syringe 30 may be configured for interacting with a corresponding plurality of expansion pockets 62 on the pressure jacket 16. In use, such as during an injection procedure where fluid is delivered from the syringe 30, the projections 100 are configured to prevent axial movement of the syringe 30 in a distal direction when fluid is being discharged from the syringe 30 under injection pressure. As the sidewall 38 of the syringe 30 expands radially outward under pressure, the projections 100 move radially outward with movement of the sidewall 38 to engage with the expansion pocket 62. In this manner, the syringe 30 becomes engaged with the pressure jacket 16 by a surface-to-surface contact between the protrusions 100 with the expansion pocket 62 and between an exterior surface of the sidewall 38 of the syringe 30 with the interior surface 28 of the sidewall 24 of the pressure jacket 16. Due to such surface-to-surface contact, the syringe 30 is prevented from moving axially in the distal direction under the proximally directed force of the piston 19.

Figure 9A:
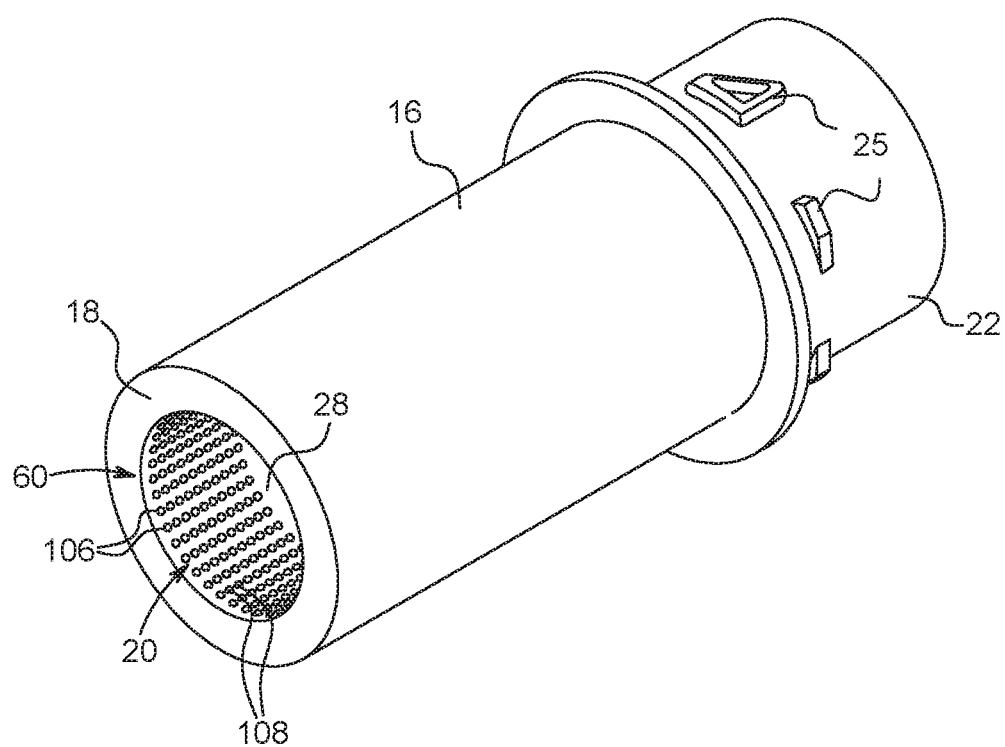
FIG. 9A is a front perspective view of a pressure jacket having a syringe retaining element in accordance with another example of the present disclosure.
Figure 9B:
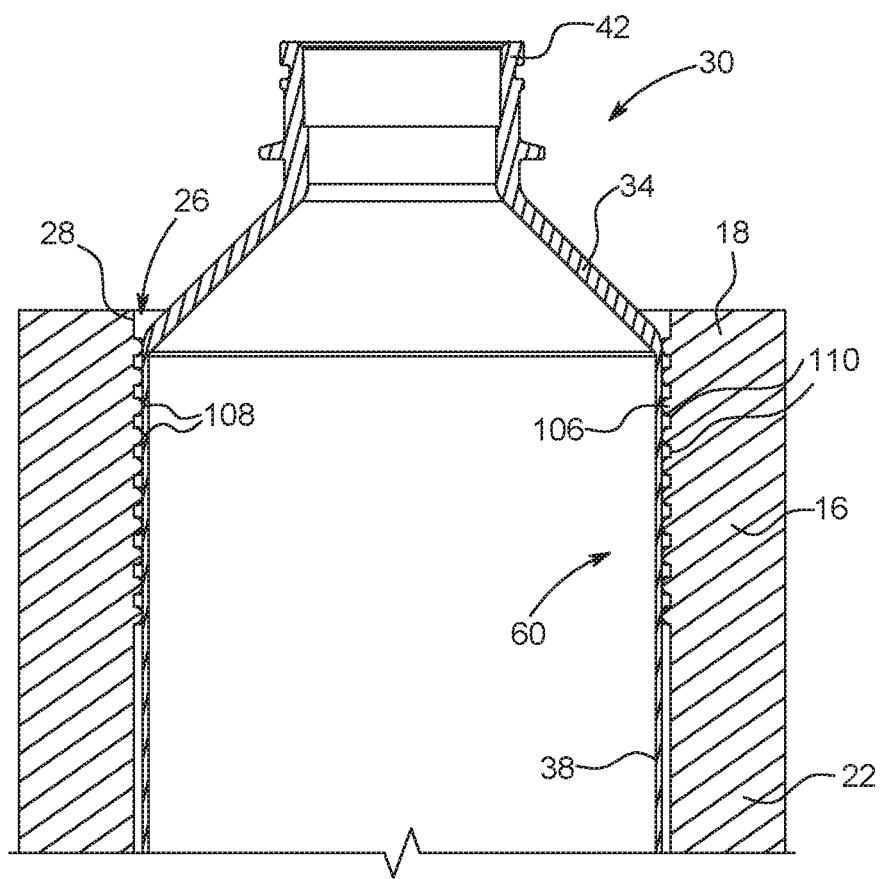
FIG. 9B is a side cross-sectional view of the pressure jacket shown in FIG. 9A in use with a syringe.

With reference to FIGS. 9A-9B, the at least one syringe retention member 60 is configured as an array of nubs 106, each of which protrudes radially inward from the interior surface 28 of the sidewall 24 of pressure jacket 16. The nubs 106 are spaced apart from each other around the circumference of the interior surface 28 of the sidewall 24 of pressure jacket 16 at equal or unequal radial intervals. In some examples, the nubs 106 have a semi-spherical shape with equal or unequal diameters. In other examples, the nubs 106 may have a semi-ovoidal or semi-ellipsoidal shape. In other examples, the nubs 106 may have any regular or irregular geometric shape. The nubs 106 may be arranged in a plurality of radial bands 108 that are axially spaced apart from one another. The radial bands 108 may be separated from one another by equal or unequal axial distance.

In use, such as during an injection procedure where fluid is delivered from the syringe 30, the nubs 106 are configured to prevent axial movement of the syringe 30 in a distal direction when fluid is being discharged from the syringe 30. As the sidewall 38 of the syringe 30 expands radially outward under pressure, the sidewall 38 of the syringe 30 resiliently deforms to fill the voids 110 between the nubs 106. In this manner, the syringe 30 becomes engaged with the pressure jacket 16 by a surface-to-surface contact between the nubs 106 and the interior surface 28 of the sidewall 24 of pressure jacket 16 with the sidewall 38 of the syringe 30. Due to such surface-to-surface contact, the syringe 30 is prevented from moving axially in the distal direction under the proximally directed force of the piston 19.

Figure 10:
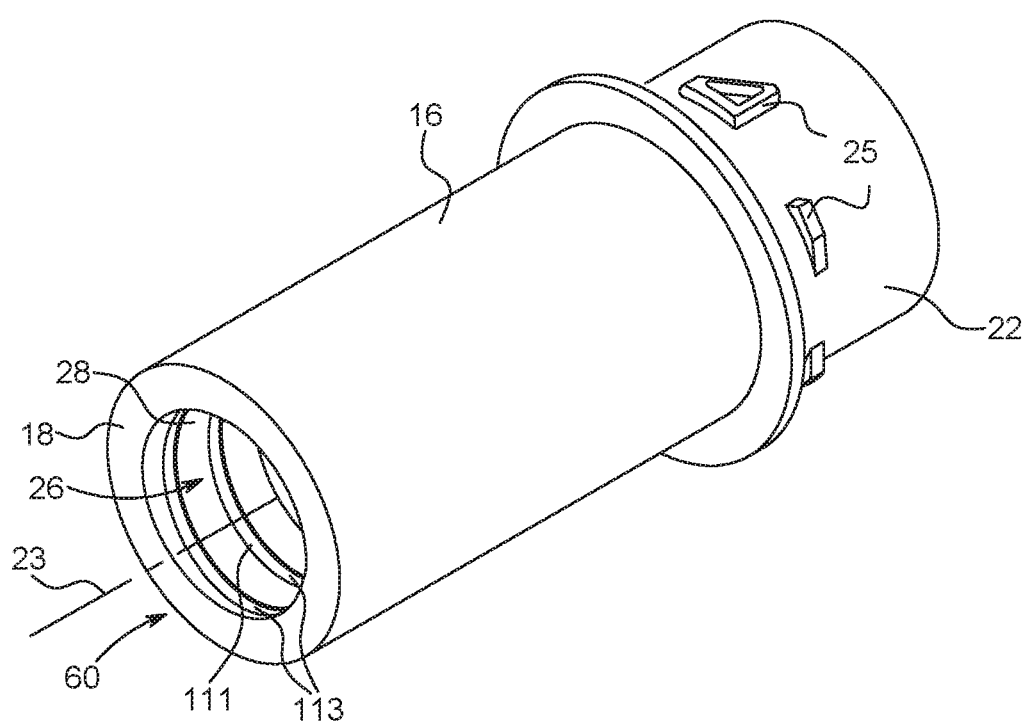
FIG. 10 is a front perspective view of a pressure jacket having a syringe retaining element in accordance with another example of the present disclosure.

With reference to FIG. 10, the at least one syringe retention member 60 is formed as a helical member 111 that protrudes radially outward into the interior surface 28 of the sidewall 24 of the pressure jacket 16. In some examples, the helical member 111 is formed as a projection that extends radially inward from the interior surface 28 of the sidewall 24 of pressure jacket 16. The helical member 111 may extend in a counterclockwise or a clockwise direction between the distal end 18 and the proximal end 22 along the longitudinal axis 23 of the pressure jacket 16. The helical member 111 may extend over at least a portion of the longitudinal length of the pressure jacket 16. The helical member 111 may have an equal or unequal pitch between successive turns 113. In use, the helical member 111 is configured to prevent axial movement of the syringe 30 (shown in FIGS. 4A-4B) in a distal direction when fluid is being discharged from the syringe 30 under injection pressure. As the sidewall 38 of the syringe 30 expands radially outward under pressure, the sidewall 38 of the syringe 30 resiliently deforms to engage the recess (or projection) defined by the helical member 111. In this manner, the syringe 30 becomes engaged with the pressure jacket 16 by a surface-to-surface contact between the helical member 111 and the interior surface 28 of the sidewall 24 of pressure jacket 16 with the sidewall 38 of the syringe 30. Due to such surface-to-surface contact, the syringe 30 is prevented from moving axially in the distal direction under the proximally directed force of the piston 19 (shown in FIG. 3).

Figure 11A:
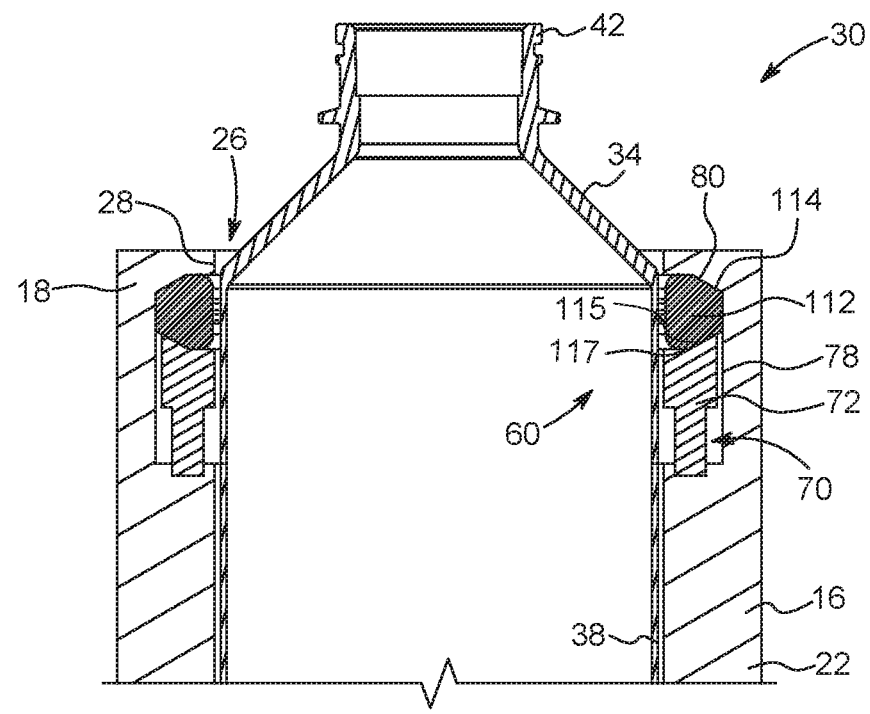
FIG. 11A is a side cross-sectional view of a pressure jacket having a syringe retaining element in accordance with another example of the present disclosure, with the syringe retaining element shown in a disengaged state or position.
Figure 11B:
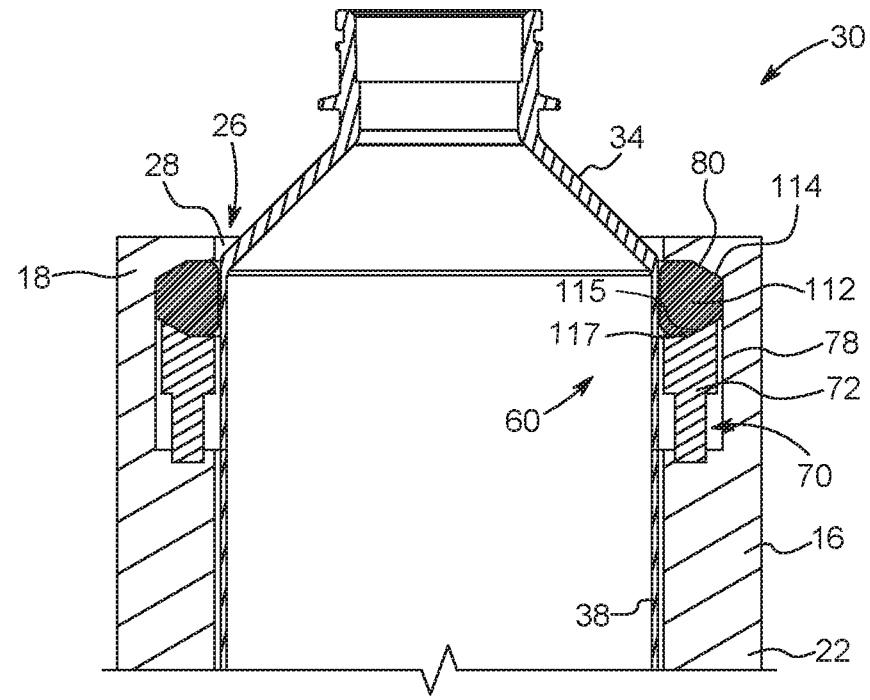
FIG. 11B is a side cross-sectional view of the pressure jacket shown in FIG. 11A, with the syringe retaining element shown in an engaged state or position.

With reference to FIGS. 11A-11B, the pressure jacket 16 may have at least one syringe retaining element 60 that is configured for movement between a disengaged position or state (FIG. 11A) and an engaged position or state (FIG. 11B) due to movement of an actuation mechanism 70. In various examples, the actuation mechanism 70 may be a mechanical mechanism, an electrical mechanism, an electromechanical mechanism, a pneumatic mechanism, a hydraulic mechanism, or a combination of any of these mechanisms. In some examples, the actuation mechanism 70 may be a rod 72 that is movable axially relative to the pressure jacket 16. The rod 72 may be movable axially relative to the pressure jacket 16 by a solenoid or a mechanical linkage arrangement operatively connected to the piston 19 (shown in FIG. 3). The compressible ring 112 is operatively connected with the actuation mechanism 70 such that movement of the actuation mechanism 70 between the disengaged position or state and the engaged position or state also moves the compressible ring 112 between a disengaged position (FIG. 11A) and an engaged position (FIG. 11B).

With continued reference to FIGS. 11A-11B, the at least one syringe retaining element 60 has the compressible ring 112 at least partially positioned within a pocket 78 extending radially outward into the interior surface 28 of the pressure jacket 16. The compressible ring 112 is circumferentially continuous around a circumference of the interior surface 28 of the sidewall 24 of pressure jacket 16. The compressible ring 112 may be made from an elastomeric material that is resiliently deformable by contact with the actuation mechanism 70.

With continued reference to FIGS. 11A-11B, the pocket 78 has a first inclined surface 80 at its distal end that guides the movement of the compressible ring 112 between the disengaged position and the engaged position. The first inclined surface 80 may be configured to guide the compressible ring 112 radially inward relative to the interior surface 28 of the pressure jacket 16. In some examples, the compressible ring 112 may have a second inclined surface 114 that corresponds to the first inclined surface 80 of the pocket 78. In use, the second inclined surface 114 of the compressible ring 112 is configured to engage the first inclined surface 80 of the pocket 78 such that the compressible ring 112 is compressed between the actuation mechanism 70 and the first inclined surface 80, thereby displacing at least a portion of the compressible ring 112 radially inward from the disengaged position (FIG. 11A) and the engaged position (FIG. 11B). Similarly, the distal end of the rod 72 may have a third inclined surface 115 configured to guide the proximal surface of the compressible ring 112 inward. In certain examples, the compressible ring 112 may have a fourth inclined surface 117 on its proximal surface that corresponds to the third inclined surface 115 of the rod 72. In use, the fourth inclined surface 117 of the compressible ring 112 is configured to engage the third inclined surface 115 of the rod 72 such that the compressible ring 112 is compressed between the actuation mechanism 70 and the third inclined surface 115. As the sidewall 38 of the syringe 30 expands radially outward under pressure, the sidewall 38 of the syringe 30 contacts the compressible ring 112 and the interior surface 28 of the pressure jacket 16. In this manner, the syringe 30 becomes engaged with the pressure jacket 16 by a surface-to-surface contact between the compressible ring 112 and the interior surface 28 of the sidewall 24 of pressure jacket 16 with the sidewall 38 of the syringe 30. Due to such surface-to-surface contact, the syringe 30 is prevented from moving axially in the distal direction under the proximally directed force of the piston 19 (shown in FIG. 1).

Figure 12A:
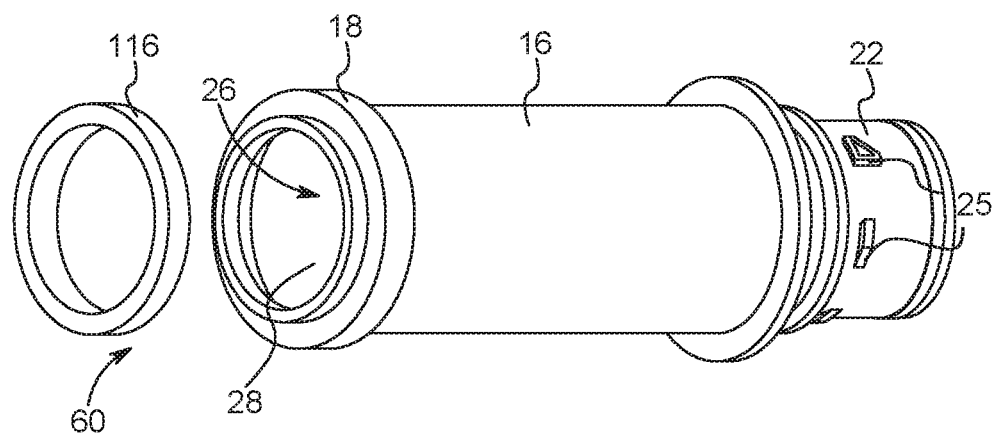
FIG. 12A is an exploded front perspective view of a pressure jacket having a syringe retaining element in accordance with another example of the present disclosure.
Figure 12B:
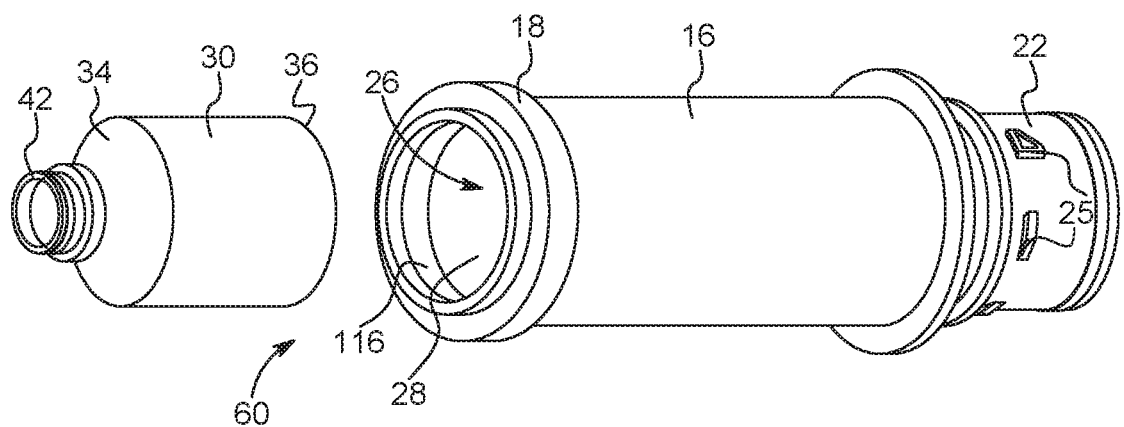
FIG. 12B is a front perspective view of the pressure jacket shown in FIG. 12A and a syringe for use therewith.
Figure 12C:
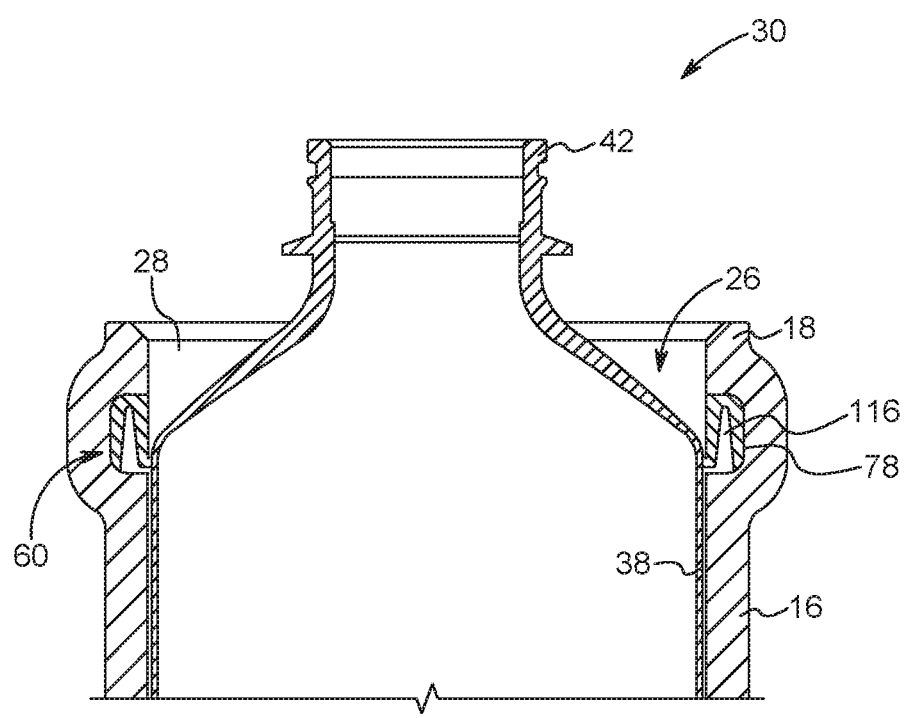
FIG. 12C is a side cross-sectional view of the pressure jacket and syringe of FIGS. 12A-12B showing the syringe retained within the pressure jacket.

With reference to FIGS. 12A-12C, the pressure jacket 16 has a lip seal 116 at least partially positioned within a pocket 78 extending radially outward into the interior surface 28 of the pressure jacket 16. The lip seal 116 is circumferentially continuous around a circumference of the interior surface 28 of the sidewall 24 of pressure jacket 16. The lip seal 116 may be made from an elastomeric material and is configured for surface-to-surface contact with the distal end 34 of the syringe 30 when the syringe 30 is inserted into the throughbore 26 of the pressure jacket 16. The lip seal 116 is configured to prevent fluid from the syringe 30 from entering into the space between the exterior surface of the syringe 30 and the interior surface 28 of the pressure jacket 16. For example, in many cases the frictional force between the sidewall 24 of pressure jacket 16 and the sidewall 38 of the syringe 30 may be reduced if liquid from the syringe seeps between the contact points between the syringe 30 and the pressure jacket 16. This effect may be eliminated or reduced by the lip seal 116.

Figure 13A:
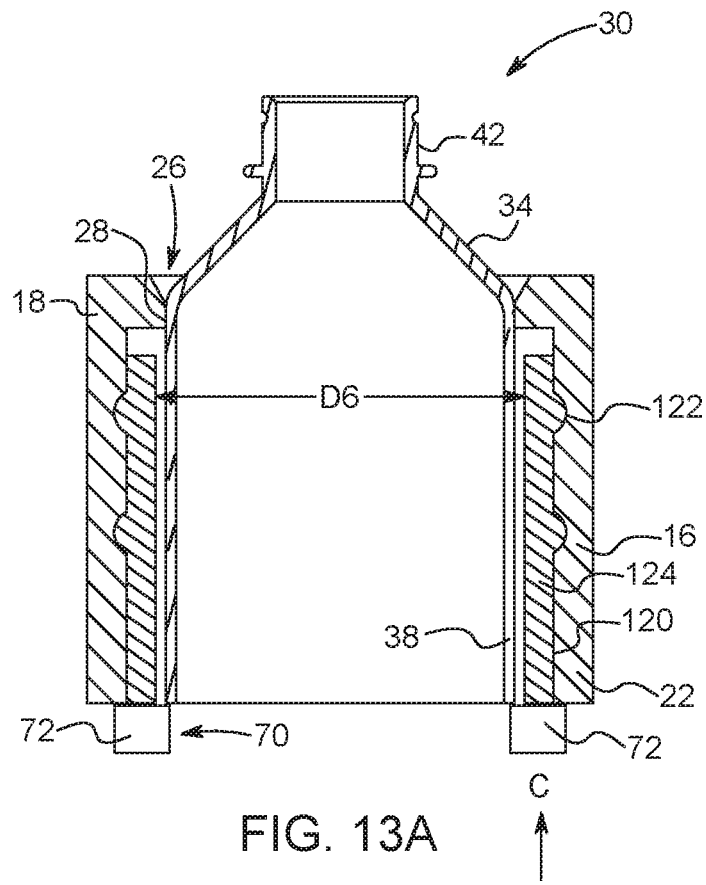
FIG. 13A is a side cross-sectional view of a pressure jacket having a syringe retaining element in accordance with another example of the present disclosure, wherein the syringe retaining element is in a disengaged state or position.
Figure 13B:
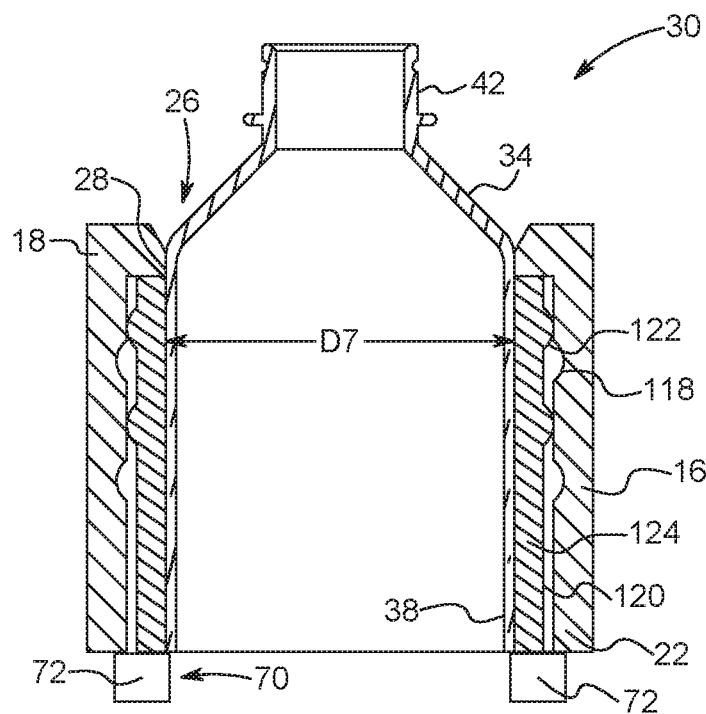
FIG. 13B is a side cross-sectional view of the pressure jacket and syringe shown in FIG. 13A, wherein the syringe retaining element is in an engaged state or position.

With reference to FIG. 13A-13B, the pressure jacket 16 may have at least one syringe retaining element 60 that is recessed radially outward into the interior surface 28 of the sidewall 24 of pressure jacket 16 to define at least one recess 118. In some examples, the at least one recess 118 may be circumferentially continuous around a circumference of the interior surface 28 of the sidewall 24 of pressure jacket 16. In other examples, the at least one recess 118 may be discontinuous in a circumferential direction around the circumference of the interior surface 28 of the sidewall 24 of pressure jacket 16. In some examples, two or more recesses 118 may be axially spaced apart from one another.

With continued reference to FIGS. 13-13B, the at least one syringe retaining element 60 may have a sleeve 120 received within the throughbore 26 of the pressure jacket 16 and positioned between the interior surface 28 of the sidewall 24 of pressure jacket 16 and the exterior surface of the sidewall 38 of the syringe 30. The sleeve 120 may have at least one groove 122 that protrudes radially outward relative to a body 124 of the sleeve 120. In some examples, the at least one groove 122 may be circumferentially continuous around a circumference of the sleeve 120. In other examples, the at least one groove 122 may be discontinuous in a circumferential direction around the circumference of the sleeve 120.

The sleeve 120 is axially movable relative to the pressure jacket 16, such as by an actuation mechanism 70, between a first position (FIG. 13A) and a second position (FIG. 13B). In various examples, the actuation mechanism 70 may be a mechanical mechanism, an electrical mechanism, an electromechanical mechanism, a pneumatic mechanism a hydraulic mechanism, or a combination of any of these mechanisms. In some examples, the actuation mechanism 70 may be a rod 72 that is movable axially relative to the pressure jacket 16 to engage a proximal end of the sleeve 120. The rod 72 may be movable axially relative to the pressure jacket 16 by a solenoid or a mechanical linkage arrangement operatively connected to the piston 19 (shown in FIGS. 4A-4B).

The at least one groove 122 is configured for being received within the at least one recess 118 on the pressure jacket 16 when the sleeve 120 is in the first position (FIG. 13A). With the sleeve 120 in the first position, a clearance space is provided between an interior surface of the sleeve 120 and the exterior surface of the syringe 30 to permit a ready insertion of the syringe 30 within the pressure jacket 16. When the sleeve 120 is moved axially in the distal direction (arrow C in FIG. 13A), the at least one groove 122 is displaced from the at least one recess 118, thereby reducing an internal diameter of the sleeve 120 from a first diameter D6 (shown in FIG. 13A), to a second diameter D7 (shown in FIG. 13B) that is smaller than the first diameter D6. With the at least one sleeve 120 is the second position, the interior surface of the sleeve 120 is in surface-to-surface contact with the exterior surface of the syringe 30. Due to such surface-to-surface contact, the syringe 30 is prevented from moving axially in the distal direction under the proximally directed force of the piston 19. In this manner, movement of the syringe 30 in the distal direction relative to the pressure jacket 16 can be prevented.

Figure 14:
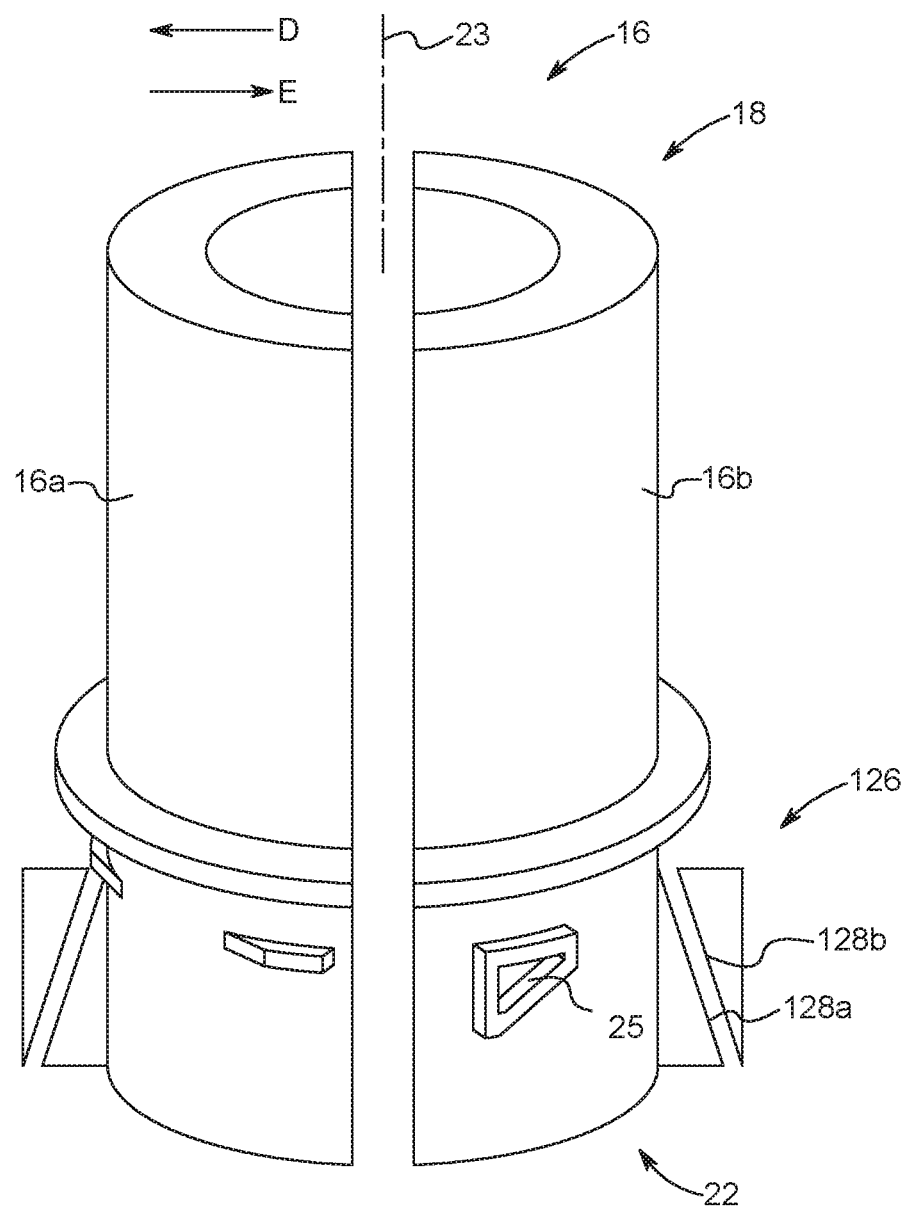
FIG. 14 is a side cross-sectional view of a pressure jacket having a syringe retaining element in accordance with another example of the present disclosure.

With reference to FIG. 14, in another embodiment, the pressure jacket 16 may have a first portion 16a and at least one second portion 16b separable from the first portion 16b in a plane along the longitudinal axis 23 of the pressure jacket 16. The first portion 16a and the at least one second portion 16b are movable relative to one another in a first direction (arrow D) to increase a space therebetween and allow for insertion of the syringe 30 (shown in FIGS. 4A-4B) within the throughbore 26. The first portion 16a and the at least one second portion 16b are also movable in a second direction (arrow E) to decrease a space therebetween and engage the exterior surface of the syringe 30 in a surface-to-surface contact with at least a portion of the interior surface 28 of the sidewall 24 of pressure jacket 16.

With continued reference to FIG. 14, a guide mechanism 126 is provided on the pressure jacket 16 and/or the injector 10 (shown in FIGS. 1-2). The guide mechanism 126 is configured for guiding the movement of the first and at least one second portions 16a, 16b of the pressure jacket 16 between a first position, wherein the first and at least one second portions 16a, 16b are separated from one another to allow insertion or removal of the syringe 30 from the pressure jacket 16, and a second position, wherein the first and at least one second portions 16a, 16b are moved toward each other to engage the syringe 30 therebetween. In some examples, the guide mechanism 126 may have a first ramp 128a on the exterior of at least one of the first and at least one second portions 16a, 16b and a second ramp 128b movable relative to the first ramp 128a. By moving the second ramp 128b relative to the first ramp 128a, the first and at least one second portions 16a, 16b can be moved closer together or further apart from one another. With the first and at least one second portions 16a, 16b of the pressure jacket 16 in the second position, the interior surface 28 of the pressure jacket 16 is in surface-to-surface contact with the exterior surface of the syringe 30. Due to such surface-to-surface contact, the syringe 30 is prevented from moving axially in the distal direction under the proximally directed force of the piston 19 (shown in FIG. 1). In this manner, movement of the syringe 30 in the distal direction relative to the pressure jacket 16 can be prevented.

Figure 15A:
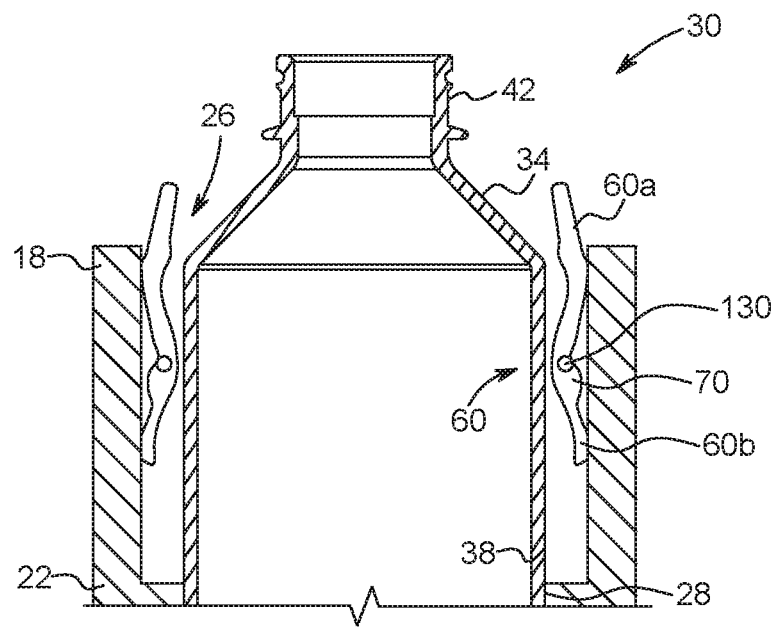
FIG. 15A is a side cross-sectional view of a pressure jacket having a syringe retaining element in accordance with another example of the present disclosure, with the syringe retaining element shown in a disengaged state or position.
Figure 15B:
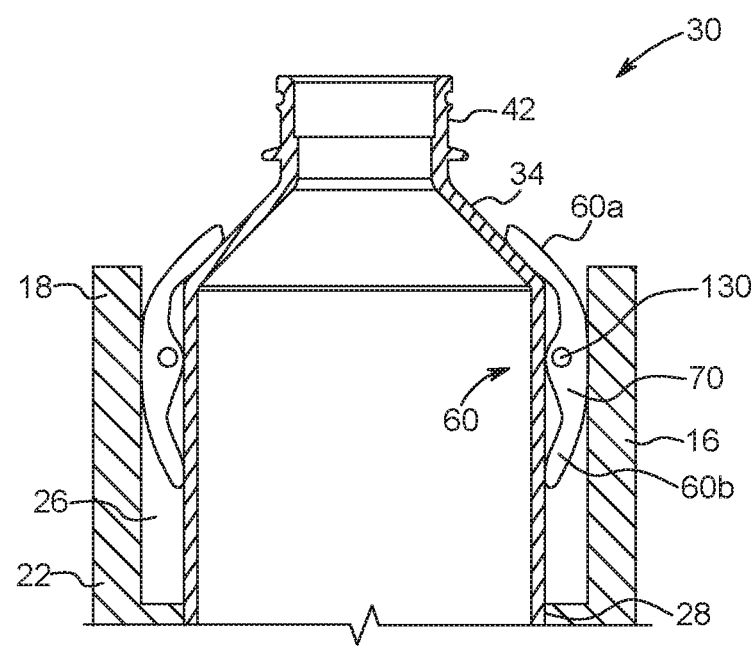
FIG. 15B is a side cross-sectional view of the pressure jacket shown in FIG. 15A, with the syringe retaining element shown in an engaged state or position.

With reference to FIGS. 15A-15B, in one embodiment, the pressure jacket 16 has at least one syringe retaining element 60 that is configured for movement between a disengaged position or state (FIG. 15A) and an engaged position or state (FIG. 15B) due to movement of an actuation mechanism 70. In some examples, at least one pair of syringe retaining elements 60 is provided opposite one another. The actuation mechanism 70 may be configured to rotate at least a portion of the at least one syringe retaining element 60 about a pivot point 130.

With continued reference to FIGS. 15A-15B, the at least one syringe retaining element 60 has a first portion 60a extending in a first direction away from the pivot point 130 and a second portion 60b extending in a second direction away from the pivot point 130. In some examples, the first and second portions 60a, 60b may be connected to one another such that they pivot together around the pivot point 130. In other examples, the first and second portions 60a, 60b may be independently pivotable about the pivot point 130. The at least one syringe retaining element 60 is operatively connected with the actuation mechanism 70 such that movement of the actuation mechanism 70 causes the at least one syringe retaining element 60 to move between a disengaged position (FIG. 15A) and an engaged position (FIG. 15B). In the disengaged position, the first portion 60a is positioned away from the throughbore 26 to prevent interference between the at least one syringe retaining element 60 and the syringe 30 during insertion and removal of the syringe 30 from the throughbore 26. In the engaged position, the at least one syringe retaining element 60 is rotated about the pivot point 130 to move the first portion 60a radially inward to engage at least a portion of the frusto-conical distal end 34 of the syringe 30. In the engaged position, at least a portion of the second end 60b is configured to be extended radially inward into the throughbore 26 of the pressure jacket 16 to contact at least a portion of the sidewall 38 of the syringe 30. During an injection procedure, radial expansion of the syringe 30 increases a contacting force between the sidewall 38 of the syringe 30 and the second portion 60b to limit or prevent axial movement of the syringe 30 relative to the pressure jacket 16. Such axial movement of the syringe 30 is further limited or prevented by interaction of the first portion 60a with the frusto-conical distal end 34 of the syringe 30.

In some examples, the at least one syringe retention member 60 may be movable within the sidewall 24 of the pressure jacket 16. For example, the at least one syringe retention member 60 may be in the form of a movable member, such as an "e-clip", that is movable within the throughbore 26 with movement of the syringe sidewall 38. When the syringe 30 is pressurized, such as during an injection procedure, the movable member may move into a groove (not shown) on the interior surface 28 of the sidewall 24 of pressure jacket 16. In this manner, the movable member can be immobilized to define a surface against which the syringe sidewall 38 can be restrained to prevent or limit axial movement of the syringe 30 within the pressure jacket 16. In other examples, the at least one syringe retaining element 60 may be a movable element that is movable into the sidewall of the pressure jacket 16 during insertion of the syringe 30 but moves out of the sidewall as the syringe sidewall 38 is expanded against the interior surface 28 of the sidewall 24 of pressure jacket 16 during a fluid injection procedure. Such movable member may be a ball that moves radially outward when the syringe 30 is inserted but moves radially inward when the syringe 30 is pressurized and acted upon by the piston 19.

Figure 16:
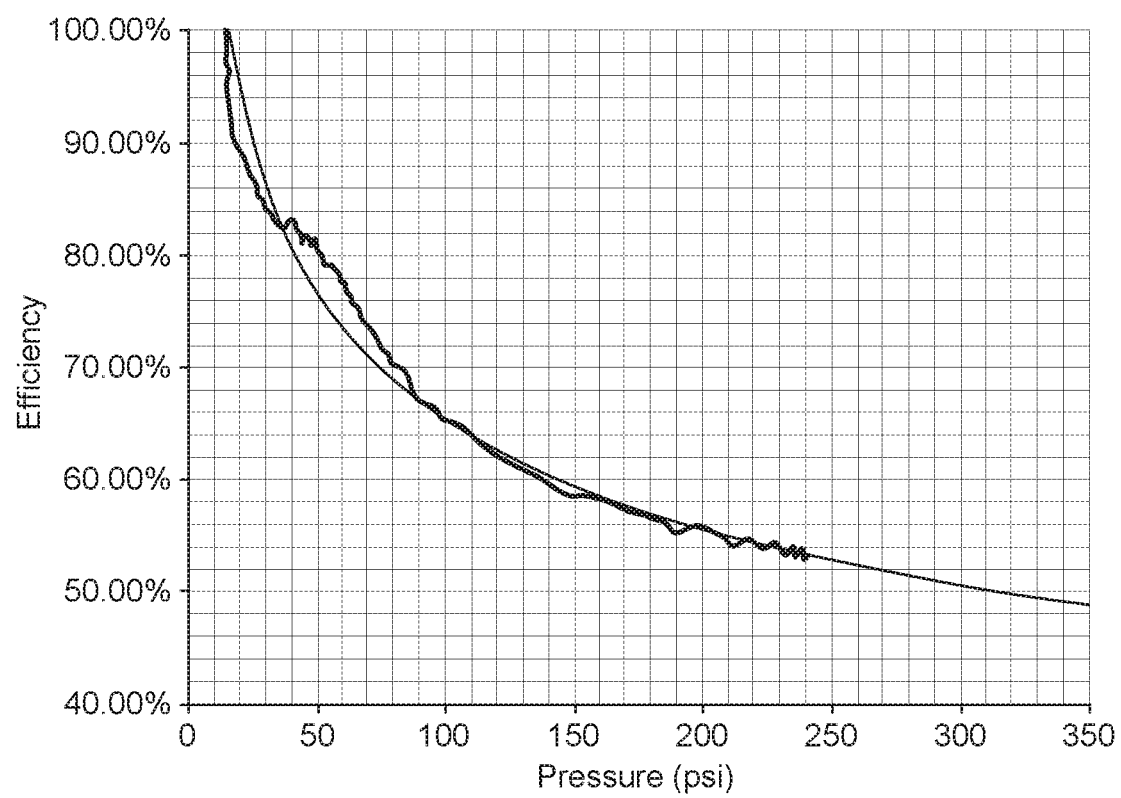
FIG. 16 is a graph showing an axial load transfer efficiency as a function of pressure in accordance with one example of the present disclosure.

With reference to FIG. 16, load transfer efficiency of a pressure jacket 16 having at least one syringe retaining element 60 according to one embodiment of the present disclosure is shown as a function of fluid pressure inside the syringe 30. The X-axis in the graph shown in FIG. 16 represents the pressure (in psi) within the syringe 30, while the Y-axis represents a percentage of axial load on the syringe 30 imposed by the piston 19 that is transferred to the distal end of the syringe 30. The amount of load absorbed by the interaction between the pressure jacket with the at least one syringe retaining element 60 and the syringe is shown as P=100−Y, where Y is the efficiency value. At low pressures (<50 psi), the axial frictional force at the surface-to-surface interface between the exterior of the syringe 30 and the interior surface 28 of the pressure jacket 16, including the surface-to-surface contact between the exterior of the syringe 30 and the at least one syringe retaining element 60, is insufficient to absorb most of the axial load on the syringe 30. For example, at 50 psi, approximately 80% of the pressure is transferred to the distal end of the syringe 30 and only 20% is absorbed by the interaction between the pressure jacket and the syringe. As shown in FIG. 16, at high pressures. Such as 200 psi, the radial expansion of the syringe 30 against the interior surface 28 of the pressure jacket 16 and the consequent engagement between the exterior surface of the syringe 30 with the at least one syringe retaining element 60 transfers 45% or more of the axial load imposed on the syringe 30 to the pressure jacket 16. In this manner, approximately 55% of the axial load on the syringe 30 is transferred to the holding bracket 44. Extrapolating to fluid pressures exceeding 300 psi, the pressure jacket 16 and the at least one syringe retaining element 60 absorb approximately 50% of the axial load imposed on the syringe 30 to the pressure jacket 16.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

We claim:

1. A pressure jacket configured to removably connect to an injector head of a fluid injector, the pressure jacket comprising:
    an open distal end, an open proximal end, and a sidewall defining a throughbore extending between the open distal end and the open proximal end along a longitudinal axis, the throughbore configured to receive at least a portion of a syringe, wherein the open distal end includes a syringe receiving opening having a diameter equal to a diameter of the throughbore and configured to receive the syringe into the pressure jacket; and
    at least one syringe retaining element positioned at least partially within the throughbore, wherein the at least one syringe retaining element comprises at least one expansion pocket on an interior surface of the sidewall of the pressure jacket;
    wherein the at least one expansion pocket is configured to engage at least a portion of a cylindrical sidewall of the syringe during pressurized delivery of fluid from the syringe due to radial expansion of the cylindrical sidewall of the syringe to prevent or limit a distal movement of the syringe relative to the pressure jacket.

2. The pressure jacket of claim 1, wherein the at least one expansion pocket is recessed radially outward into the interior surface of the sidewall of the pressure jacket.

3. The pressure jacket of claim 2, wherein a volume of the at least one expansion pocket is selected to prevent plastic yield of the cylindrical sidewall of the syringe during the pressurized delivery of fluid from the syringe exceeding a predetermined threshold pressure.

4. The pressure jacket of claim 2, wherein a volume of the at least one expansion pocket is selected to maintain a predetermined axial restraining force due to radial expansion of at least the portion of the cylindrical sidewall of the syringe into the at least one expansion pocket during the pressurized delivery of fluid from the syringe.

5. The pressure jacket of claim 2, wherein the at least one expansion pocket is circumferentially continuous around a circumference of the interior surface of the sidewall of the pressure jacket.

6. The pressure jacket of claim 2, wherein the at least one expansion pocket comprises a plurality of expansion pockets axially offset from each other along the longitudinal axis of the pressure jacket.

7. The pressure jacket of claim 2, wherein the at least one expansion pocket comprises one or more through holes that extend through the sidewall of the pressure jacket.

8. The pressure jacket of claim 2, wherein the at least one expansion pocket is circumferentially discontinuous around a circumference of the interior surface of the sidewall of the pressure jacket.

9. The pressure jacket of claim 1, wherein the at least one syringe retaining element further comprises at least one protrusion protruding radially inward from the interior surface of the sidewall of the pressure jacket.

10. The pressure jacket of claim 9, wherein the at least one protrusion is circumferentially continuous around a circumference of the interior surface of the sidewall of the pressure jacket.

11. The pressure jacket of claim 9, wherein the at least one protrusion comprises a plurality of protrusions axially offset along the longitudinal axis of the pressure jacket.

12. The pressure jacket of claim 9, wherein the at least one protrusion is circumferentially discontinuous around a circumference of the interior surface of the sidewall of the pressure jacket.

13. The pressure jacket of claim 1, wherein the at least one expansion pocket is recessed radially outward into an interior surface of the sidewall of the pressure jacket and wherein the pressure jacket further comprises at least one protrusion protruding radially inward from the interior surface of the sidewall of the pressure jacket.

* * * * *

UNITED STATES PATENT AND TRADEMARK OFFICE
CERTIFICATE OF CORRECTION

PATENT NO. : 11,389,585 B2
APPLICATION NO. : 16/331366
DATED : July 19, 2022
INVENTOR(S) : Spohn et al.

Page 1 of 1

It is certified that error appears in the above-identified patent and that said Letters Patent is hereby corrected as shown below:

In the Specification
In Column 1, Line 36, delete "angiograph," and insert -- angiography, --, therefor.
In Column 1, Line 59, delete "w ile" and insert -- while --, therefor.
In Column 10, Line 61, delete "interior surface 26" and insert -- interior surface 28 --, therefor.
In Column 12, Line 58, delete "injector 14" and insert -- injector housing 14 --, therefor.
In Column 13, Line 24, delete "injector 14." and insert -- injector housing 14. --, therefor.
In Column 17, Line 10, delete "SA" and insert -- 5A --, therefor.
In Column 17, Line 13, delete "SA" and insert -- 5A --, therefor.
In Column 17, Line 36, delete "SA" and insert -- 5A --, therefor.
In Column 18, Line 10, delete "retractable fingers 78" and insert -- retractable fingers 76 --, therefor.
In Column 24, Line 29, delete "pneumatic mechanism" and insert -- pneumatic mechanism, --, therefor.
In Column 24, Line 51, delete "is" and insert -- in --, therefor.
In Column 24, Line 61, delete "first portion 16b" and insert -- second portion 16b --, therefor.
In Column 25, Line 66, delete "second end 60b" and insert -- second portion 60b --, therefor.

Signed and Sealed this
Eleventh Day of October, 2022

Katherine Kelly Vidal
*Director of the United States Patent and Trademark Office*